(12) United States Patent
Nakamura et al.

(10) Patent No.: US 11,555,221 B2
(45) Date of Patent: Jan. 17, 2023

(54) METHOD FOR DETECTING MOOD DISORDERS

(71) Applicants: DNA CHIP RESEARCH INC., Tokyo (JP); NATIONAL CENTER OF NEUROLOGY AND PSYCHIATRY, Tokyo (JP)

(72) Inventors: Seiji Nakamura, Tokyo (JP); Yohei Ishizawa, Tokyo (JP); Ryo Matoba, Tokyo (JP); Kenichi Matsubara, Tokyo (JP); Hiroshi Kunugi, Tokyo (JP); Hiroaki Hori, Tokyo (JP)

(73) Assignees: DNA CHIP RESEARCH INC.; National Center of Neurology and Psychiatry

( * ) Notice: Subject to any disclaimer, the term of this patent is extended or adjusted under 35 U.S.C. 154(b) by 734 days.

(21) Appl. No.: 16/335,526

(22) PCT Filed: Sep. 25, 2017

(86) PCT No.: PCT/JP2017/034437
§ 371 (c)(1),
(2) Date: Oct. 7, 2019

(87) PCT Pub. No.: WO2018/056430
PCT Pub. Date: Mar. 29, 2018

(65) Prior Publication Data
US 2020/0024663 A1 Jan. 23, 2020

Related U.S. Application Data

(60) Provisional application No. 62/398,843, filed on Sep. 23, 2016.

(51) Int. Cl.
*C12Q 1/6883* (2018.01)

(52) U.S. Cl.
CPC ..... *C12Q 1/6883* (2013.01); *C12Q 2600/158* (2013.01)

(58) Field of Classification Search
CPC ............ C12Q 1/6883; C12Q 2600/158; C12Q 1/68
See application file for complete search history.

(56) References Cited

U.S. PATENT DOCUMENTS

2006/0252068 A1* 11/2006 Lo ........................ C12Q 1/6883
435/6.11

FOREIGN PATENT DOCUMENTS

JP 5442208 B2 3/2014
WO 2004108899 A2 12/2004

OTHER PUBLICATIONS

Nakatani et al. Human Molecular Genetics. 2006. 15(12):1949-1962. (Year: 2006).*
Chen et al. Molecular & Cellular Proteomics 1.4. 2001. MCP Papers in Press. (Year: 2001).*
Kendrick et al. Kendrick Labs, Inc. Updated Sep. 25, 2014. (Year: 2014).*
Maier et al. FEBS Letters. 2009. 583:3966-3973. (Year: 2009).*
Pascal et al. BMC Genomics. 2008. 9:246. (Year: 2008).*
Chan et al. G&P magazine. 2006. 6(3): 20-26. (Year: 2006).*
Le-Niculescu et al. Molecular Psychiatry. 2021. 26:2776-2804. (Year: 2021).*
Le-Niculescu et al. Molecular Psychiatry. 2009. 14: 156-174. (Year: 2009).*
Affymetrix. Retrieved on Dec. 1, 2021 online: https://www.affymetrix.com/analysis/netaffx/showresults.affx#. (Year: 2021).*
Kerman et al. Frontiers in Neuroscience. 2012. 6:Article 135. (Year: 2012).*
International Preliminary Report on Patentability for International Application No. PCT/JP2017/034437; dated Dec. 19, 2017.
Lee Sheng-An. "Construction and analysis of the protein-protein interaction networks for schizophrenia, bipolar disorder, and major depression." BMC Bioinformatics (2011): p. 1-15.
Hori Hiroaki, et al. "Blood-based gene expression signatures of medication-free outpatients with major depressive disorder: integrative genome-wide and candidate gene analyses." Scientific reports (Jan. 2016): DOI: 10.1038/srep18776.
Watanabe Yoshifumi. "Molecular mechanism of stress-vulnerability: role of epigenetics. "Jouenal of Clinical an Experimental Medicine (Supplement), Depression-the forefront of treatment & research (Feb. 2014): p. 117-122.
Office Action issued by the Japan Patent Office dated Nov. 30, 2021 for patent application No. JP2018-540333 (Machine Translation).
Vibe Skov et al., "Gene expression profiling with principal component analysis depicts the biological continuum from essential thrombocythemia over polycythemia vera to myelofibrosis" Experimental Hematology (2012): vol. 40, p. 771-780.

* cited by examiner

*Primary Examiner* — Joseph G. Dauner
(74) *Attorney, Agent, or Firm* — Mendelsohn Dunleavy, P.C.

(57) ABSTRACT

The object of the invention is to provide a method for easily and objectively detecting mood disorders in a subject by measuring the expression levels of prescribed genes in the peripheral blood of the subject, the reliability of the detection result being high. The invention also provides a method for detecting mood disorders in a subject, the method having a step for measuring the gene expression levels of ribosomal protein genes, CDKN1C, or any combination thereof in the peripheral blood derived from the subject, and detecting whether or not the subject has mood disorders on the basis of the measurement results.

6 Claims, 18 Drawing Sheets

PCA score map
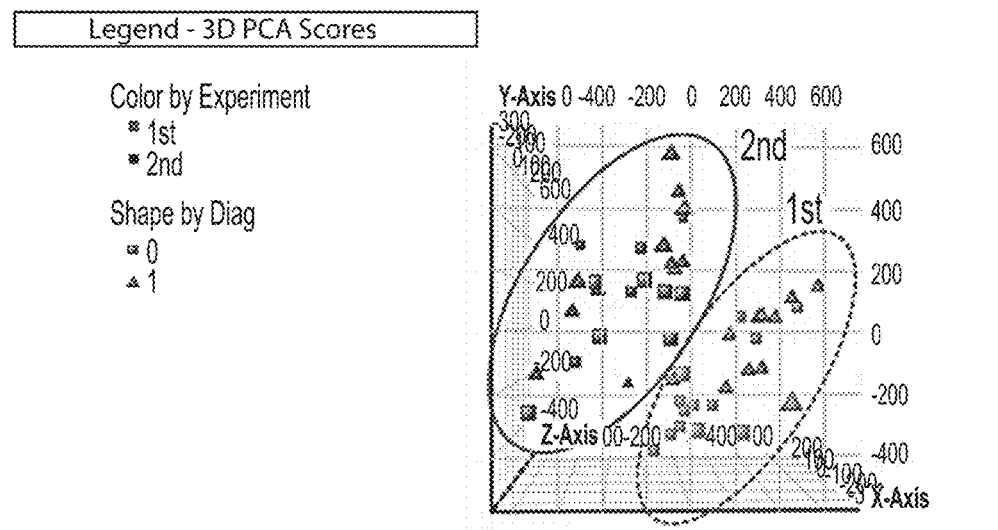
Hierarchical clustering of data before Combat correction
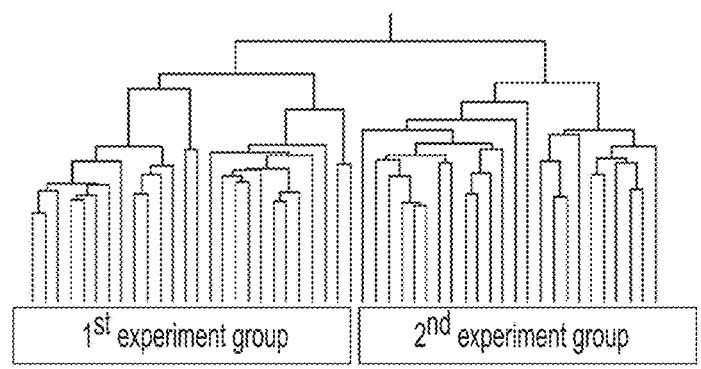
Hierarchical clustering of data after Combat correction
Fig. 1 Differences in batches of microarray experiment data Background information about specimens
|  | Mood disorders group (Major depression) | Healthy control group |
|---|---|---|
| Number of cases | 14 | 11 |
| Age | 43.4±9.5 | 41.5±15.9 |
| Gender (female %) | 50.0 | 54.5 |
| HAM-D | 20.4±9.5 | - |
qPCR Results
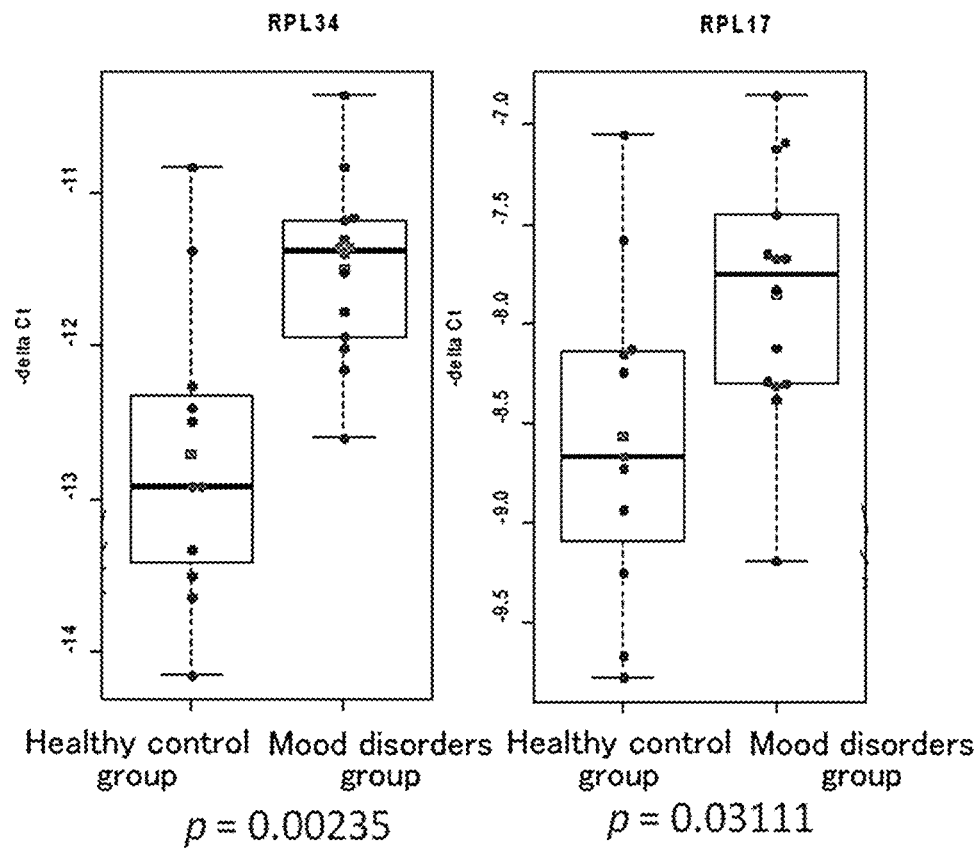
Fig. 2 Results of qPCR verification experiments Background information about specimens
|  | Healthy control group | Major depression group | Bipolar depression group | Schizophrenia group |
|---|---|---|---|---|
| Number of cases | 46 | 48 | 46 | 43 |
| Age | 37.4±4.8 | 36.8±8.7 | 36.4±8 | 37.4±9.6 |
| Gender (female %) | 52.2 | 47.9 | 50.0 | 46.5 |
| HAM-D | - | 23.8±4.8 | 21.8±5.3 | - |
qPCR Result (RPL34)
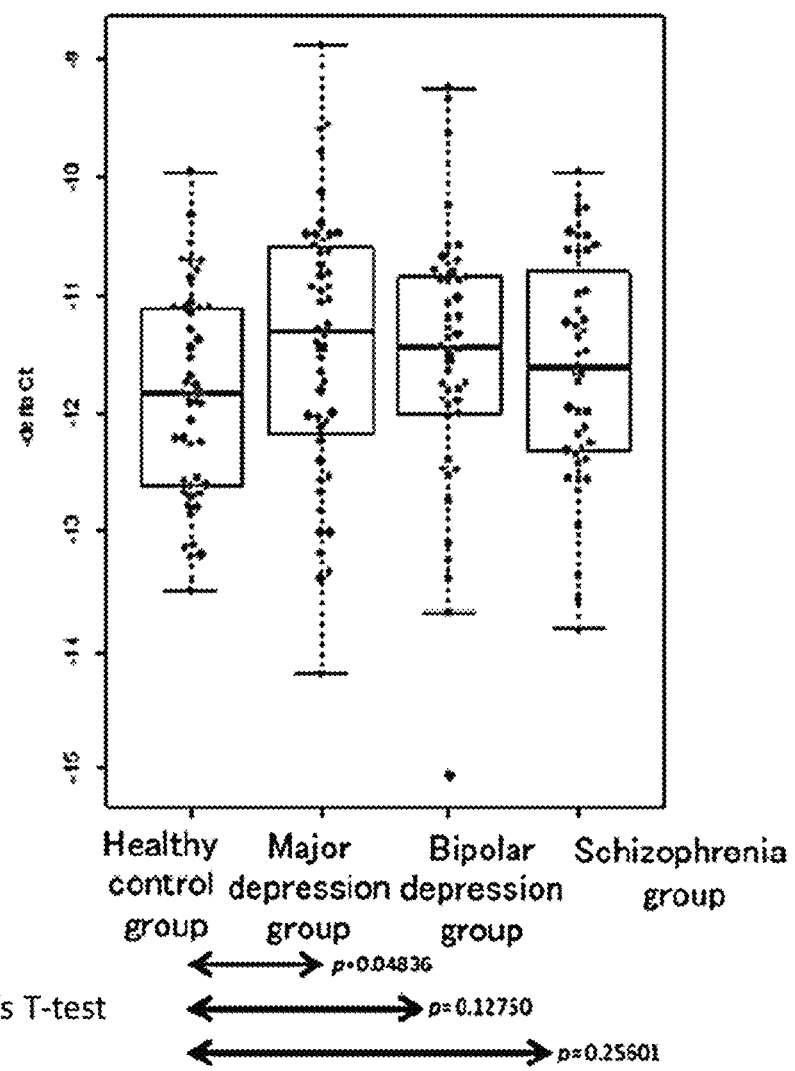
Fig. 3A Verification of possibility of differential diagnosis

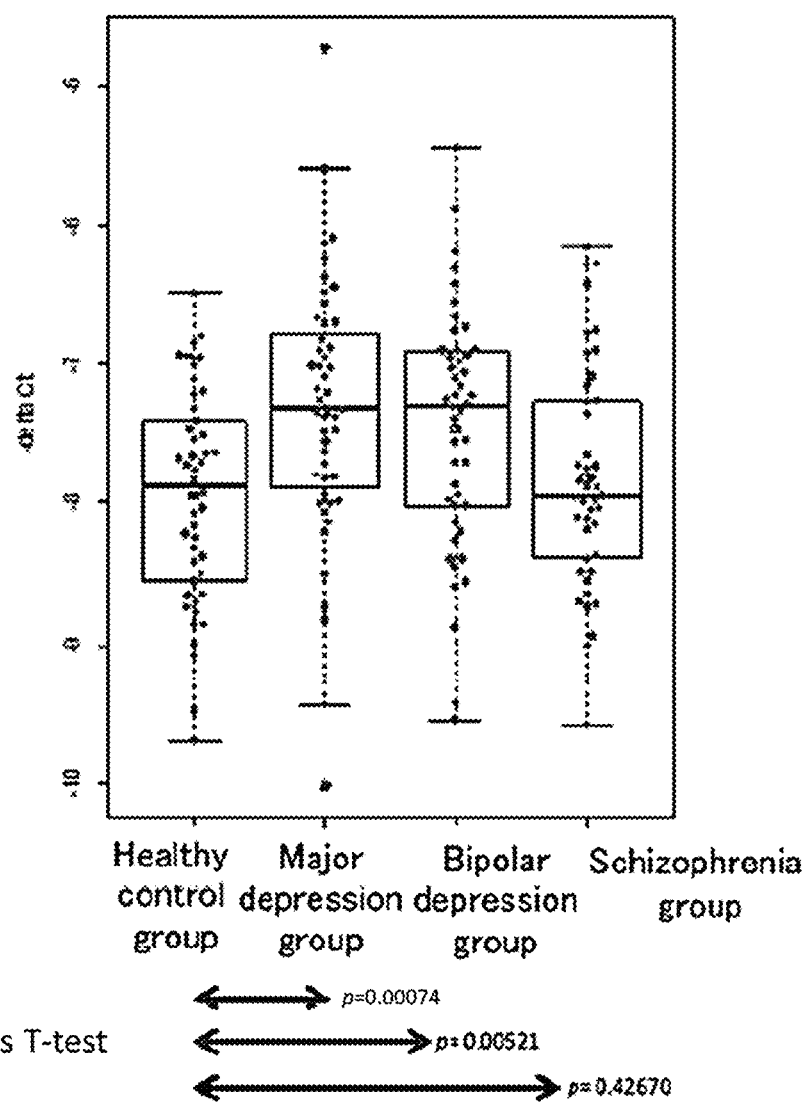
Fig. 3B Verification of possibility of differential diagnosis

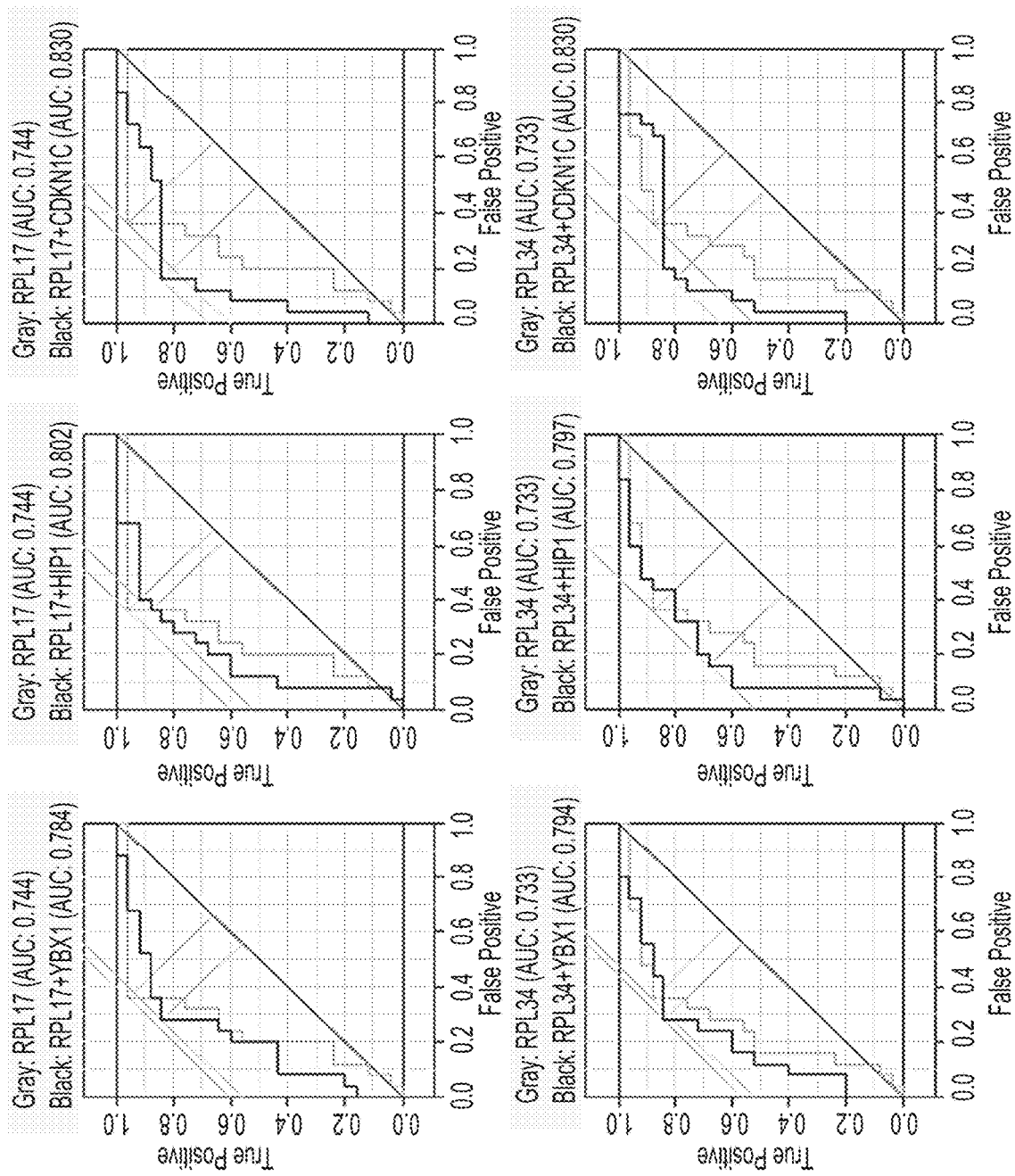
Fig. 4A ROC analyses of candidate genes supporting RPL17 or RPL34 (microarray 50 specimen data)

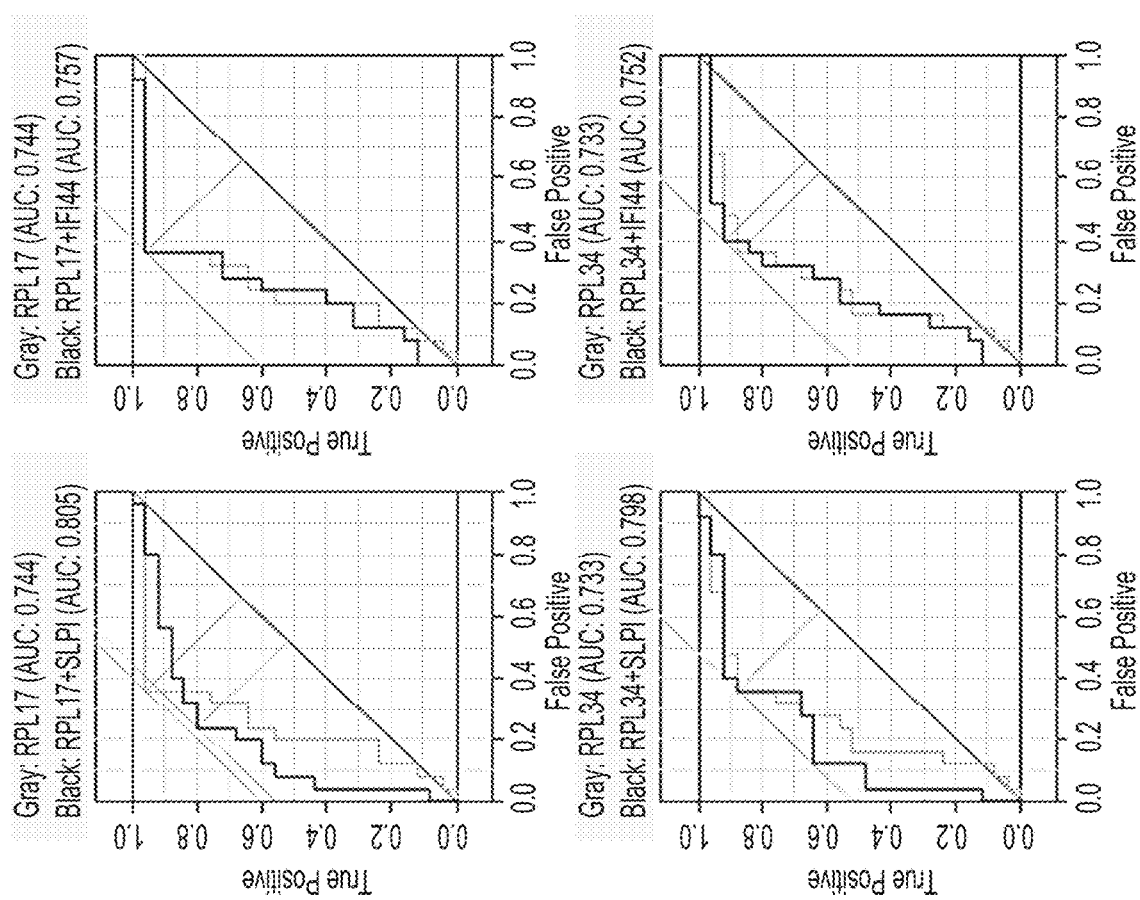
Fig. 4B ROC analyses of candidate genes supporting RPL17 or RPL34 (microarray 50 specimen data)

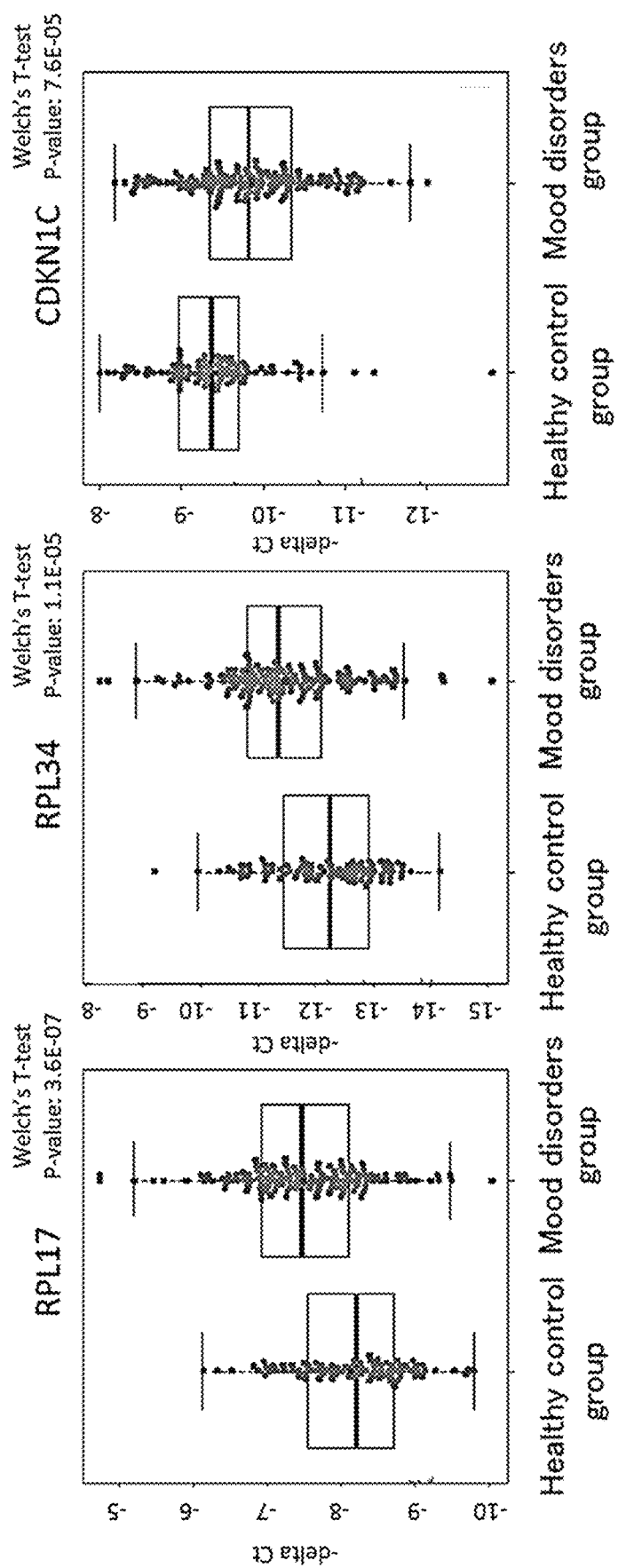
Fig. 5 qPCR results of 124 cases of mood disorders vs 82 cases of healthy controls

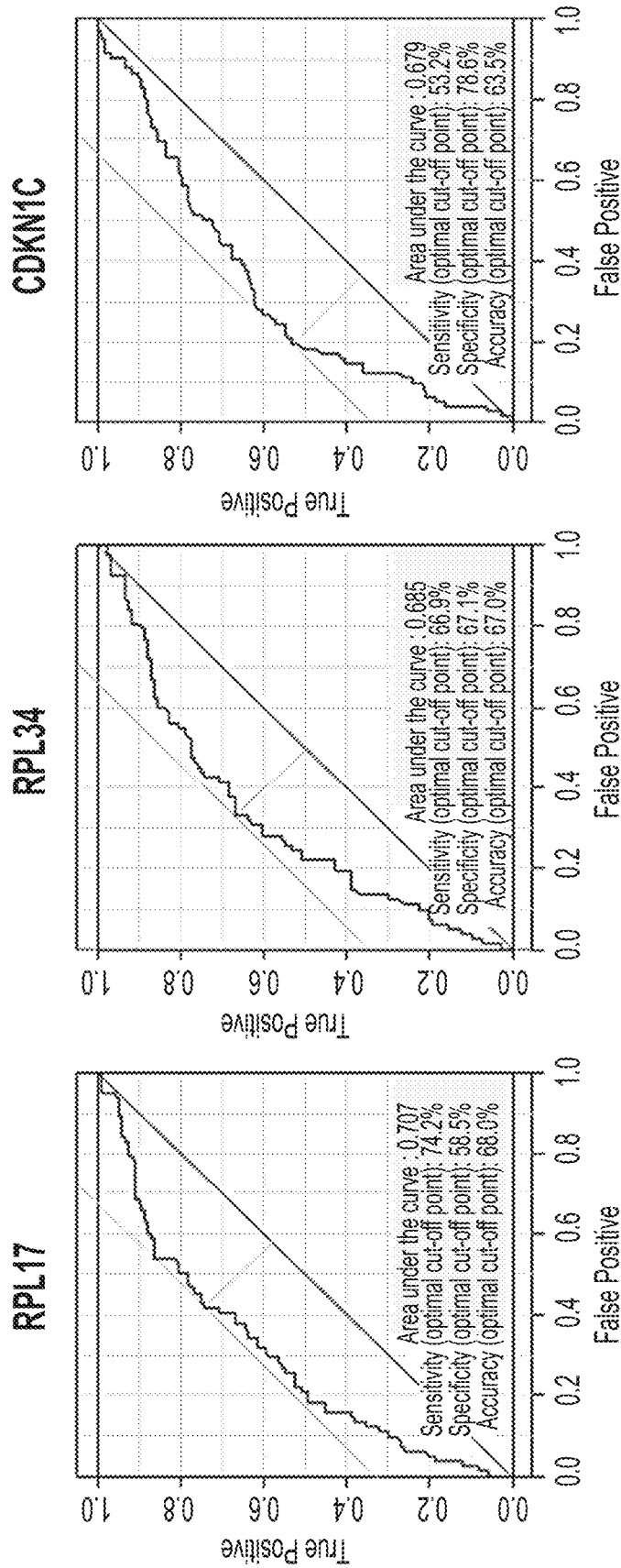
Fig. 6A Diagnostic accuracy of mood disorders by RPL17 or RPL34 + CDKN1C (qPCR results)

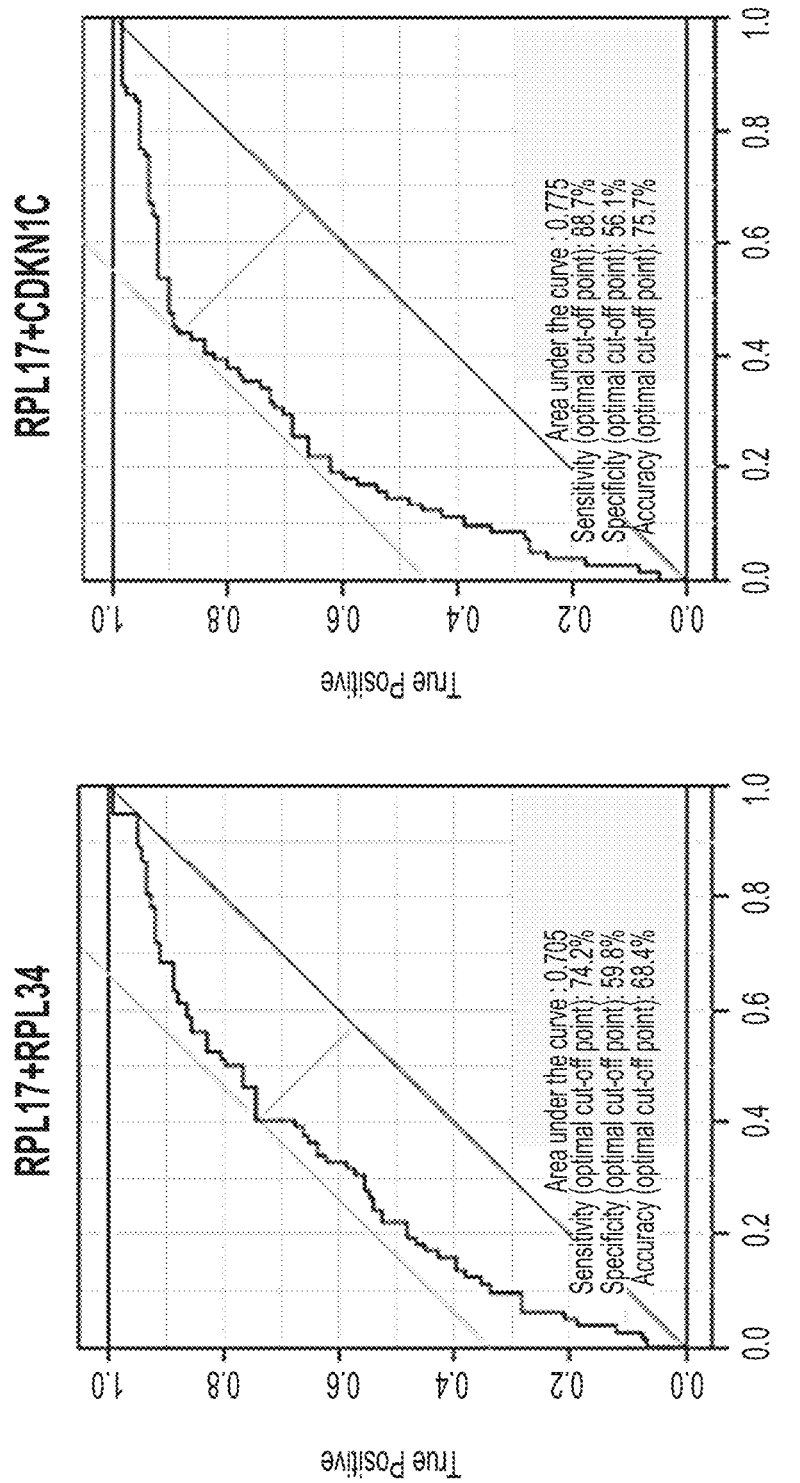
Fig. 6B Diagnostic accuracy of mood disorders by RPL17 or RPL34 + CDKN1C (qPCR results)

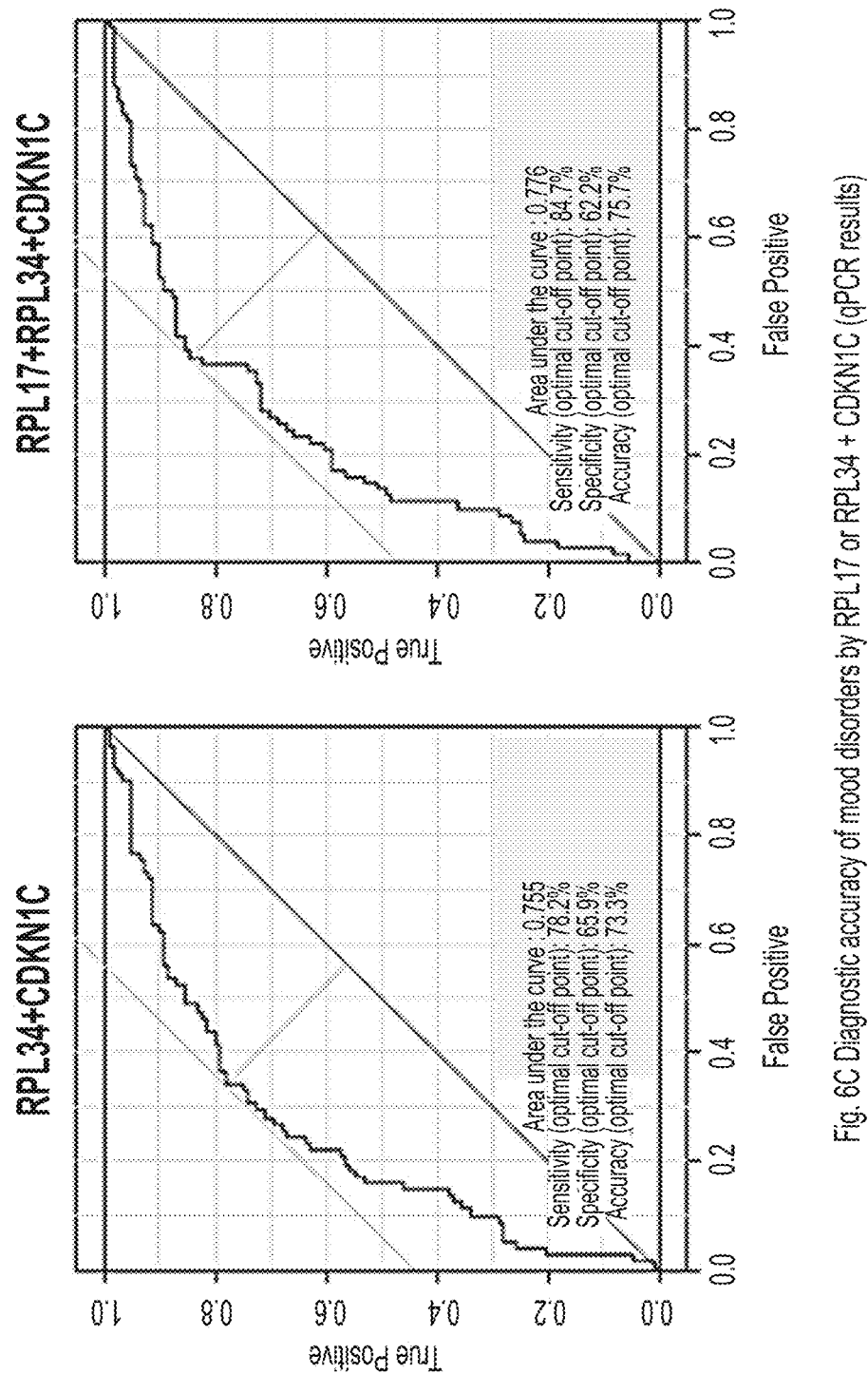
Fig. 6C Diagnostic accuracy of mood disorders by RPL17 or RPL34 + CDKN1C (qPCR results)

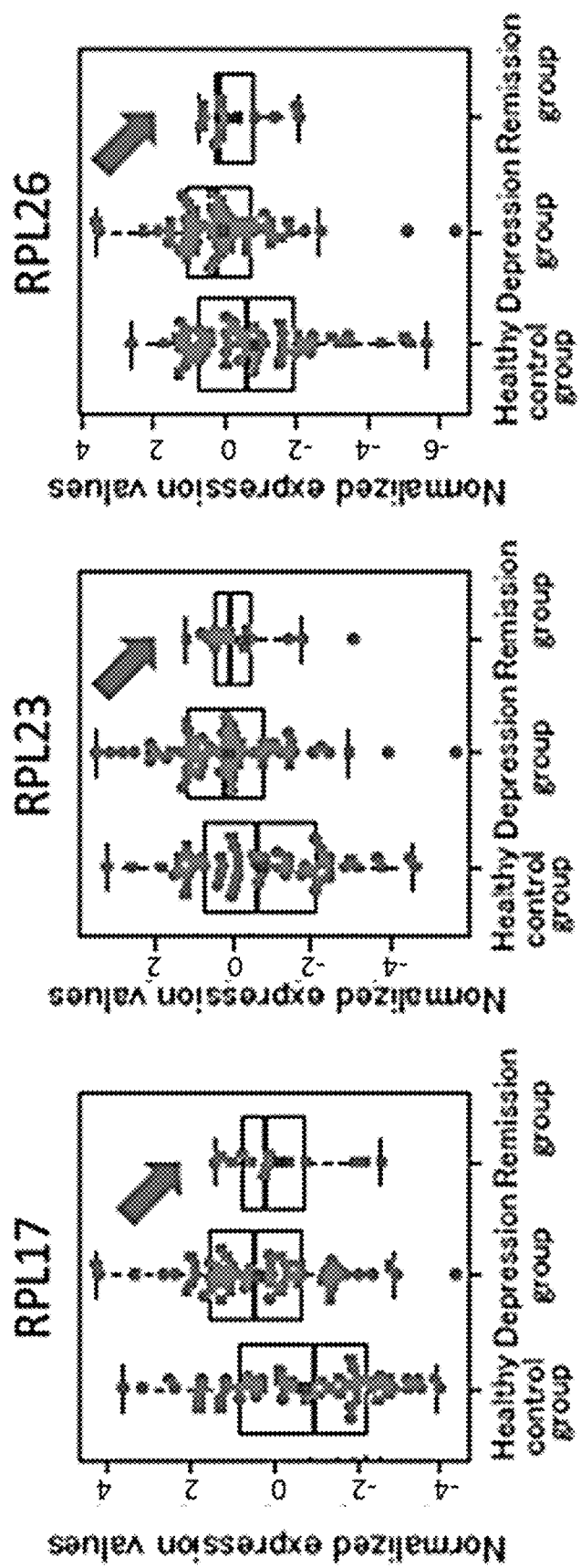
Fig. 7A Gene expression of remitted patients (microarray results)

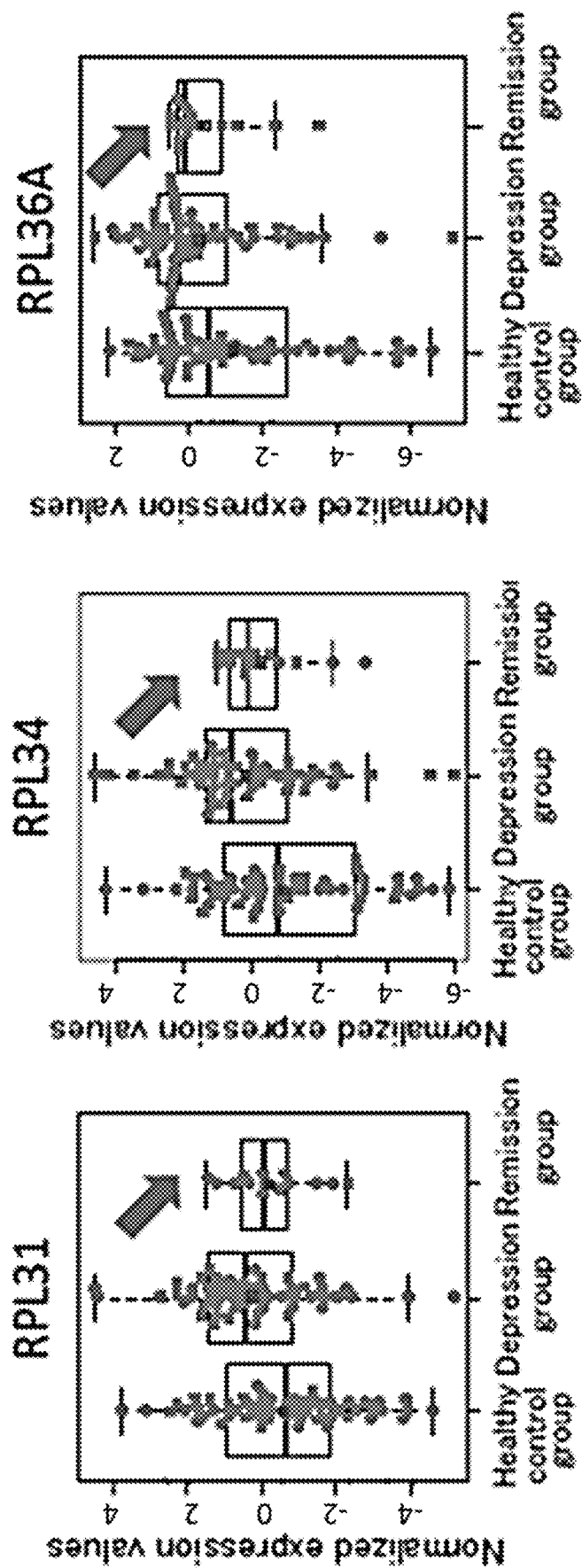
Fig. 7B Gene expression of remitted patients (microarray results)

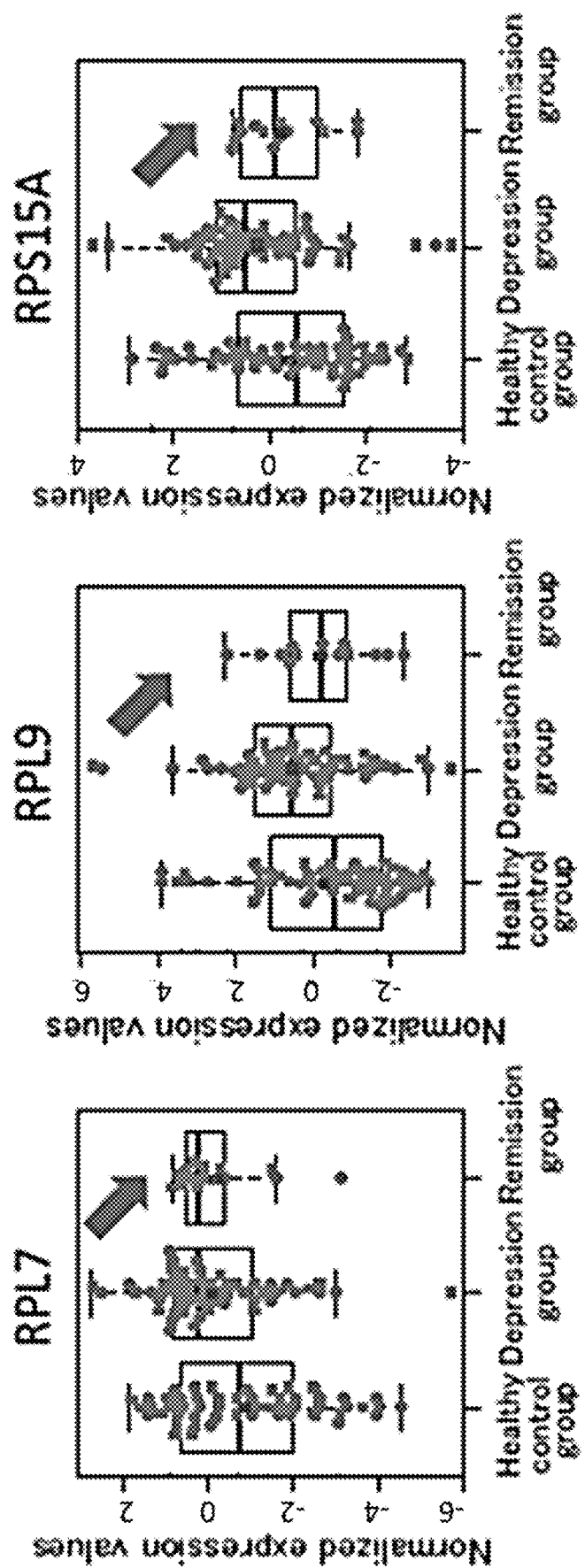
Fig. 7C Gene expression of remitted patients (microarray results)

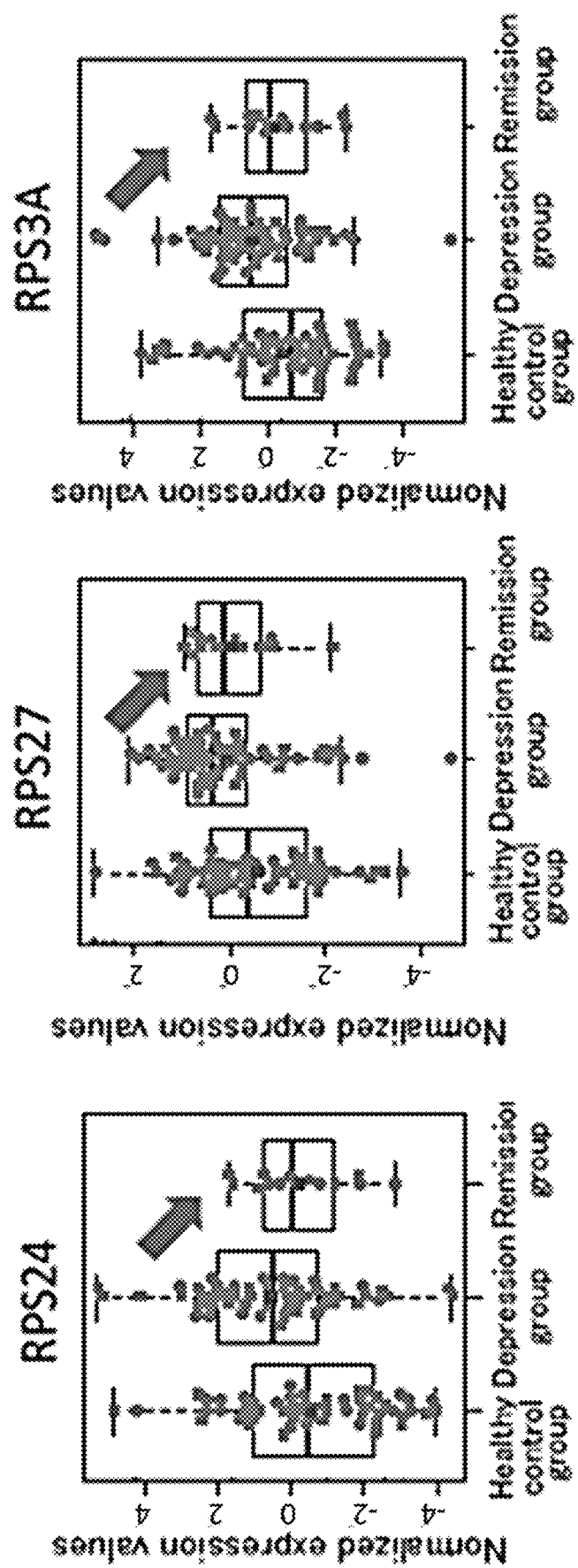
Fig. 7D Gene expression of remitted patients (microarray results)

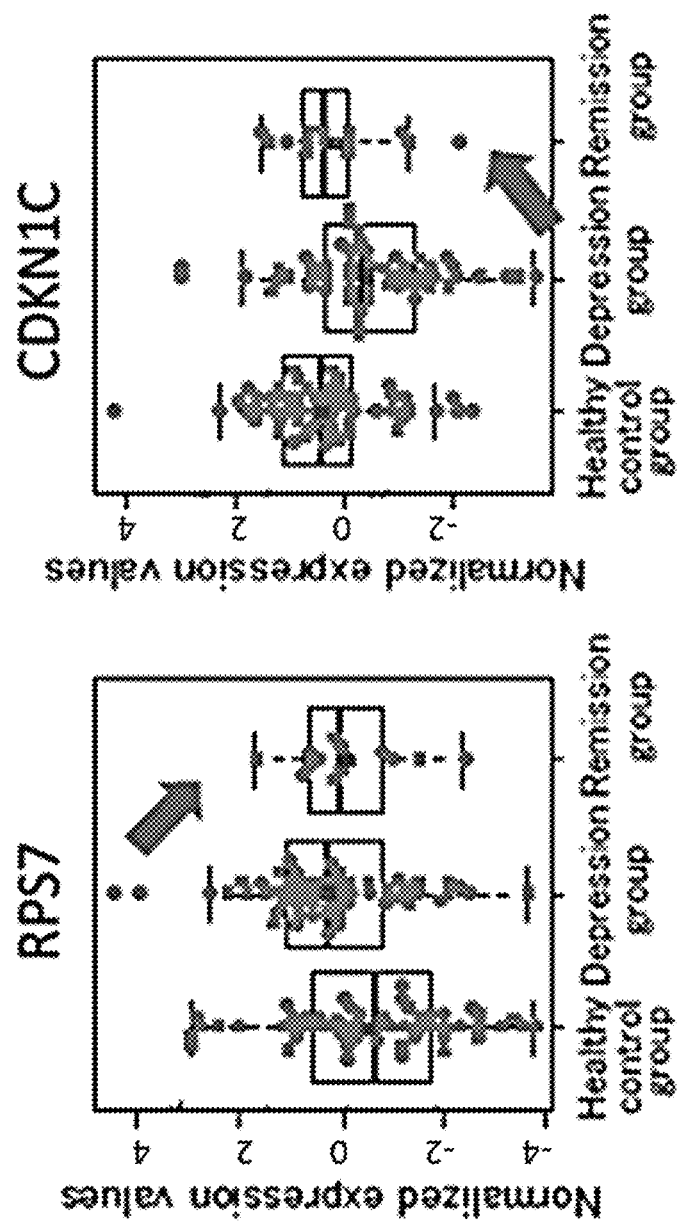
Fig. 7E Gene expression of remitted patients (microarray results)

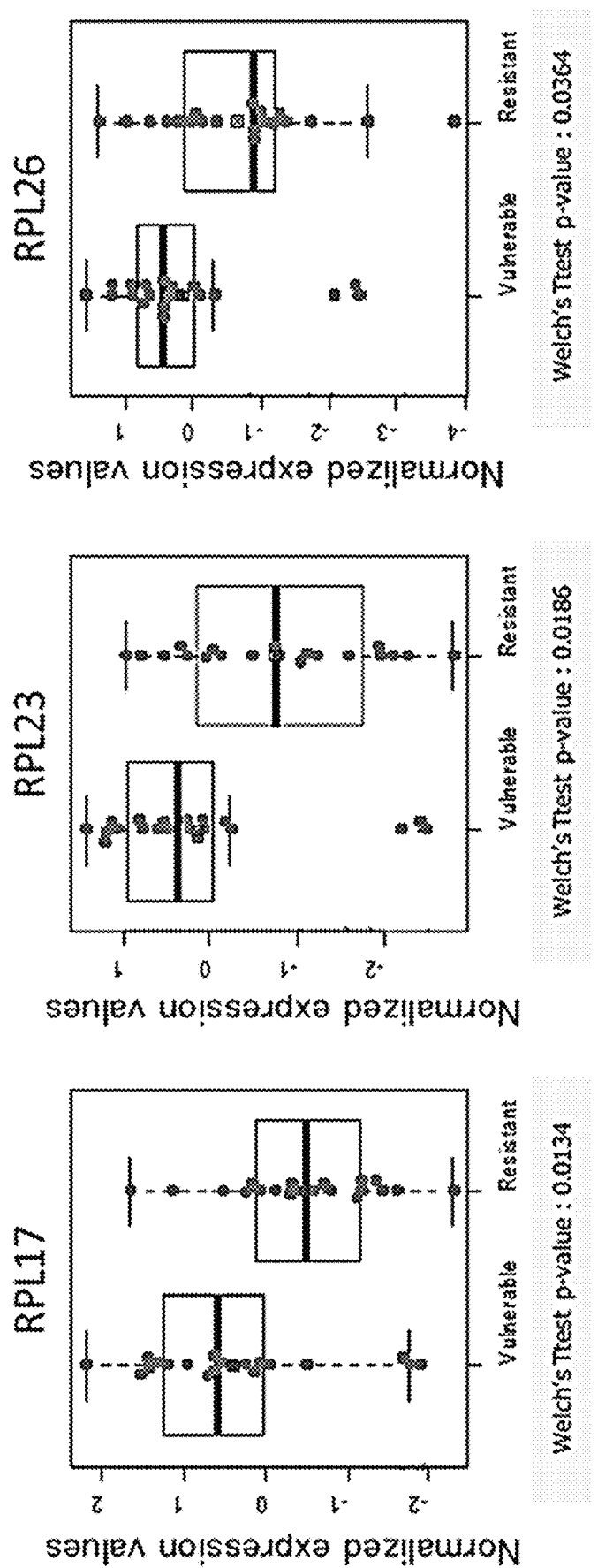
Fig. 8A Stress vulnerability and ribosomal protein genes (microarray results)

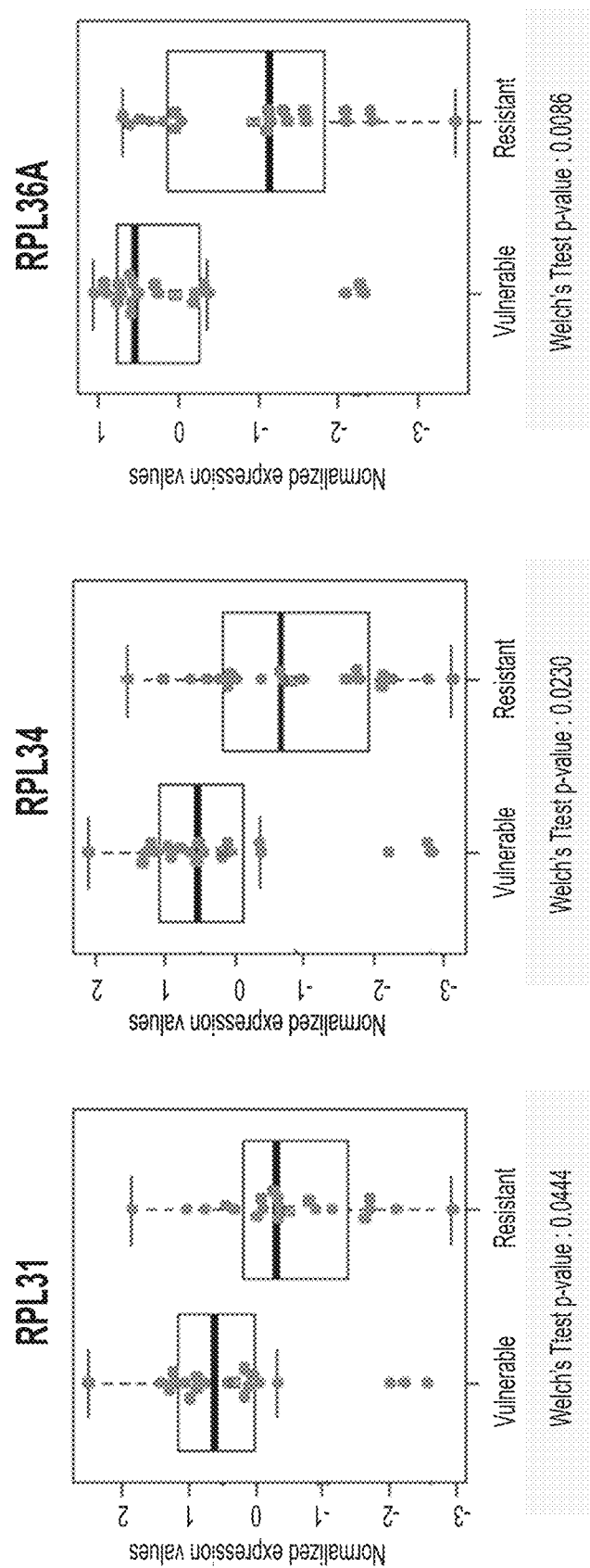
Fig. 8B Stress vulnerability and ribosomal protein genes (microarray results)

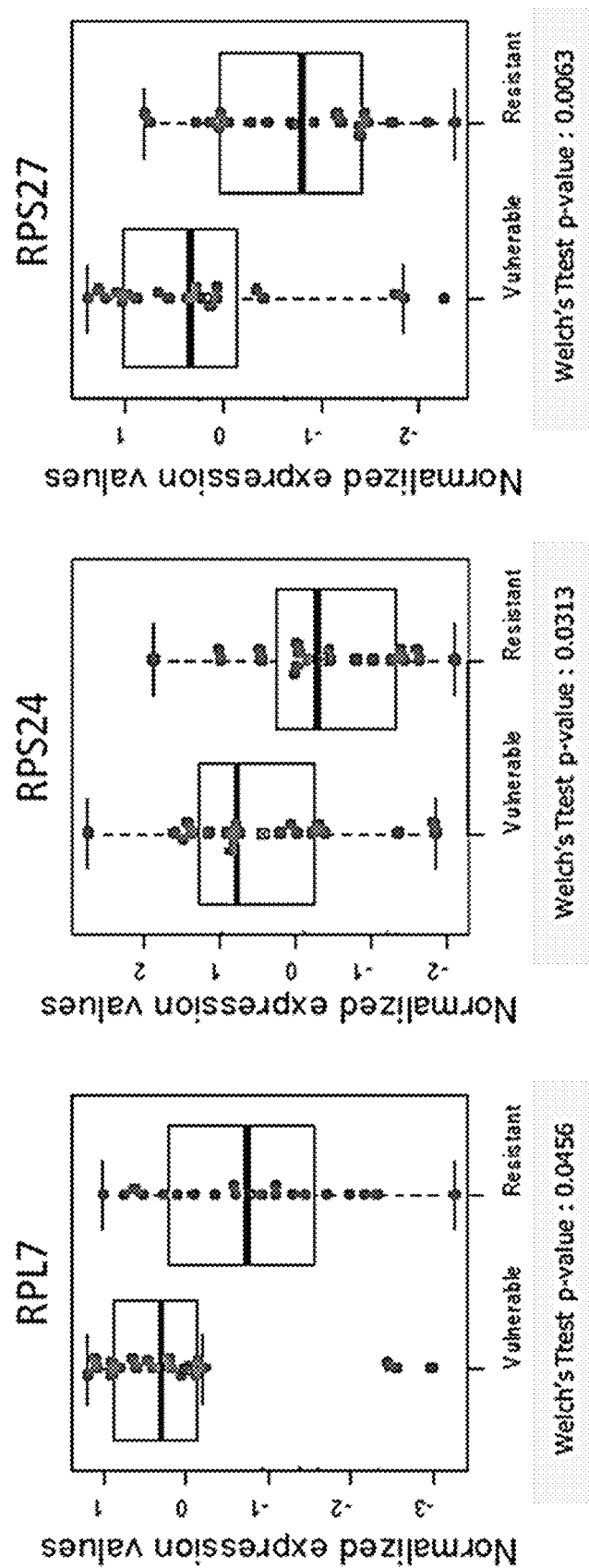
Fig. 8C Stress vulnerability and ribosomal protein genes (microarray results)

METHOD FOR DETECTING MOOD DISORDERS

CROSS REFERENCE TO RELATED APPLICATIONS

This application claims the benefit of U.S. Provisional Patent Application Ser. No. 62/398,843, filed on Sep. 23, 2016, which is incorporated herein by reference.

FIELD OF THE INVENTION

The present invention relates to a method for detecting mood disorders in a subject, and particularly to a method for detecting mood disorders by measuring the expression levels of prescribed genes using the peripheral blood of the subject.

BACKGROUND OF THE INVENTION

Mood disorder is a psychiatric illness represented by depression and has such symptoms as depressed moods, anxieties, impatience, declined mental activities, and it is also known that the symptoms of mood disorders include impaired appetite, insomnia, alcohol dependency and what not.

The mood disorders include major depression and bipolar disorders; it is reported that the lifetime prevalence exceeds 10% up to 15% these days and assumed that these rates will increase in future in consideration of stressful circumstances in the modern society. Although the mood disorder is an illness having a high incidence rate, many patients think that this illness is simply a physical malfunction, because the symptoms of the mood disorder vary and frequently appear physically, so that it is difficult to diagnose this illness accurately; furthermore this illness is related to social issues such as an increase in social withdrawal and suicide, and therefore there is an urgent need to accurately diagnose and treat mood disorders.

Conventional diagnoses of mood disorders frequently depend on evaluation made by doctors and clinical psychologists and subjective opinions of patients. As it is difficult to obtain a disease certificate on the basis of such a subjective diagnosis, some patients appeal excess symptoms, and on the other hand some patients avoid seeing physicians, because they do not want to be diagnosed as mood disorders for fear of other people's distorted views, and tend to underestimate their symptoms, so that it is difficult to diagnose mood disorders accurately. Furthermore, accurate evaluations made by physicians and clinical psychologists require skilled expertise as well as sufficient knowledge and experience about mood disorders; however, it is frequently difficult to tell physical symptoms that are not caused by mood disorders from physical symptoms caused by mood disorders.

In view of such circumstances, Japanese Patent No. 5442208, for example, proposes searching for possible causative genes of depression and using those genes in diagnosis as molecular markers.

However, since there are as many as 18 candidate genes for molecular markers searched in Japanese Patent No. 5442208 and no similarities have been found among their individual genetic functions, it cannot be ruled out that only genes changed in their expressions, which are indirectly or accidentally caused by direct functional changes associated with depression, are observed; therefore it is unknown whether or not a group of genes sharing similar biological functions change in their expression in depression. Accordingly, there is some possibility that the aforementioned search of molecular markers is insufficient or that marker genes expressed as a result of some specific functional changes of patients with depression are overlooked.

Moreover, no confirmatory analysis has been conducted in both specimens and methods as the means of searching for candidate genes, and therefore it cannot be ruled out that what was observed was genes that changed in their expressions accidentally; therefore the sensitivity and reproducibility of those molecular markers for depression is questionable, reliability being not so high.

SUMMARY OF THE INVENTION

The present invention has been made in view of the aforementioned circumstances. The object of the invention is to provide a method for easily and objectively detecting mood disorders in a subject by measuring the expression levels of prescribed genes in the peripheral blood of the subject, the reliability of the detection result being high.

The present inventors searched for genes that changed in their expressions as compared with healthy controls, using peripheral blood samples collected from mood disorder patients having pathologic depressive symptoms, to find that a group of genes including ribosomal protein genes changed in their expressions in mood disorder patients and, therefore, paid attention to the possibility of detecting mood disorders by measuring the expression levels of each of the group of genes including ribosomal protein genes.

As a result of conducting extensive research in order to solve the aforementioned problems, the present inventors found that it was possible to detect whether or not subjects were affected by mood disorders by measuring the expression levels of each of the group of genes including prescribed ribosomal protein genes in the subjects. Furthermore, they found that it is also possible to evaluate the effect of treating mood disorder patients and stress vulnerability of subjects on the basis of the aforementioned finding.

More specifically, according to a first major viewpoint of the present invention, a method for detecting a mood disorder in a subject is provided, comprising a step of measuring the expression levels of ribosomal protein genes, CDKN1C, or any combination thereof in the peripheral blood derived from the subject, wherein it is detected whether or not the subject has a mood disorder on the basis of the measurement results.

In such a constitution, a method for detecting whether or not a subject has a mood disorder can be provided conveniently and objectively, simply by measuring the expression levels of ribosomal protein genes, CDKN1C, or any combination thereof in the peripheral blood collected from the subject, wherein the reliability thereof is high.

Since it is possible to evaluate whether or not a subject has a mood disorder simply by measuring the expression levels of ribosomal protein genes, CDKN1C, or any combination thereof, the present method enables to evaluate the effect of treatment for a mood disorder patient non-invasively and conveniently, determine the stress vulnerability of the subject, and can be used for selecting treatment methods or approaches suitable for a mood disorder patient or a subject.

Moreover, according to one embodiment of the present invention, provided is the aforementioned method further comprising a step of comparing the measured expression levels with the expression base line values of the corresponding genes in the peripheral blood derived from a healthy control, wherein it is shown that the subject has a mood disorder when (i) the measured genes are ribosomal protein genes and the measured expression levels are higher than the expression base line values, or (ii) the measured gene is CDKN1C and the measured expression level is lower than the expression base line value.

Moreover, according to another embodiment of the present invention, the mood disorder is preferably major depression or bipolar disorder in the first major viewpoint of the present invention.

Moreover, according to another embodiment of the present invention, the ribosomal protein gene is preferably RPL17, RPL23, RPL26, RPL31, RPL34, RPL36A, RPL7, RPL9, RPS15A, RPS24, RPS27, RPS3A or RPS7 in the aforementioned method.

Moreover, according to another embodiment of the present invention, the measuring step preferably measures the expression levels of RPL34 and CDKN1C or the expression levels of RPL17 and CDKN1C in the aforementioned method.

Moreover, according to another embodiment of the present invention, the measuring step preferably measures the level of mRNA or cDNA of the gene or the level of protein encoded by the gene in the aforementioned first major viewpoint of the present invention.

According to a second major viewpoint of the present invention, provided is a method for determining the effect of mood disorder treatment in a mood disorder patient, the method comprising (a) a step of measuring the expression levels of ribosomal protein genes, CDKN1C, or any combination thereof in the peripheral blood derived from the mood disorder patient, wherein the effect of mood disorder treatment for the mood disorder patient is determined on the basis of the measurement results.

According to another embodiment of the present invention, provided is the method of the aforementioned second major viewpoint of the present invention, the method further comprising (b) a step of measuring the expression levels of the corresponding genes in the peripheral blood derived from the mood disorder patient after treatment and (c) a step of making a comparison between the measurement results of the step (a) and the measurement results of the step (b), wherein it is shown that the mood disorder treatment for the mood disorder patient is effective when (i) the measured genes are ribosomal protein genes and the expression levels in the step (b) are lower than the expression levels of the step (a), or (ii) the measured gene is CDKN1C and the expression level in the step (b) is higher than the expression level of the step (a).

Moreover, according to another embodiment of the present invention, in addition to the step (b) and the step (c), the following steps can further be provided: (d) a step of measuring the expression levels of the corresponding genes in the peripheral blood derived from the mood disorder patient after an additional treatment on the basis of the results of the step (c); and (e) a step of making a comparison between the measurement results of the step (b) and the measurement results of the step (d), wherein the step (d) is repeated when necessary.

Moreover, according to another embodiment of the present invention, the mood disorder is preferably major depression or bipolar disorder in the method of the aforementioned second major viewpoint of the present invention.

Moreover, according to another embodiment of the present invention, the ribosomal protein gene is preferably RPL17, RPL23, RPL26, RPL31, RPL34, RPL36A, RPL7, RPL9, RPS15A, RPS24, RPS27, RPS3A or RPS7 in the aforementioned method.

Moreover, according to another embodiment of the present invention, the step (a) preferably measures the expression levels of RPL34 and CDKN1C or the expression levels of RPL17 and CDKN1C in the aforementioned method.

According to a third major viewpoint of the present invention, a provided is a method for determining stress vulnerability of a subject, the method comprising a step of measuring the expression levels of ribosomal protein genes or any combination thereof in the peripheral blood derived from the subject, wherein it is determined whether or not the subject has stress vulnerability on the basis of the measurement results.

Moreover, according to another embodiment of the present invention, provided is the method of the aforementioned third major viewpoint of the present invention, the method further comprising a step of comparing the measured expression levels with the expression base line values of the corresponding genes in the peripheral blood derived from a stress-resistant healthy control, wherein it is shown that the subject has stress vulnerability when the measured expression levels are higher than the expression base line values.

Moreover, according to another embodiment of the present invention, the ribosomal protein gene is preferably RPL17, RPL23, RPL26, RPL31, RPL34, RPL36A, RPL7, RPS24 or RPS27.

According to a fourth major viewpoint of the present invention, provided is a genetic marker for detecting a mood disorder, the genetic marker being selected from ribosomal protein genes and CDKN1C.

Moreover, according to another embodiment of the present invention, the mood disorder is preferably major depression or bipolar disorder in the aforementioned fourth major viewpoint of the present invention.

Moreover, according to another embodiment of the present invention, the ribosomal protein gene is preferably RPL17, RPL23, RPL26, RPL31, RPL34, RPL36A, RPL7, RPL9, RPS15A, RPS24, RPS27, RPS3A or RPS7 in the aforementioned genetic marker.

According to a fifth major viewpoint of the present invention, provided is a solid support or kit for detecting a mood disorder in a subject, the solid support or kit comprising primers, probes or antibodies for confirming the genetic expression of ribosomal protein genes or CDKN1C.

Moreover, according to another embodiment of the present invention, wherein the ribosomal protein gene is preferably RPL17, RPL23, RPL26, RPL31, RPL34, RPL36A, RPL7, RPL9, RPS15A, RPS24, RPS27, RPS3A or RPS7.

According to a sixth major viewpoint of the present invention, provided is a method for determining the effect of mood disorder treatment for a mood disorder patient, the method comprising (a) a step of giving mood disorder treatment to the mood disorder patient, (b) a step of measuring the expression levels of ribosomal protein genes, CDKN1C, or any combination thereof in the peripheral blood derived from the mood disorder patient to whom treatment was given, (c) a step of comparing the measured expression levels with the expression base line values of the corresponding genes in the peripheral blood derived from a healthy control, wherein the treatment of the mood disorder patient to whom the treatment was given is continued or reinforced when (i) the measured genes are ribosomal protein genes and the measured expression levels are higher than the expression base line values, or (ii) the measured gene is CDKN1C and the measured expression level is lower than the expression base line level, or the treatment of the mood disorder patient to whom the treatment was given is discontinued or reduced when (i) the measured genes are ribosomal protein genes and the measured expression levels are lower than the expression base line values, or (ii) the measured gene is CDKN1C and the measured expression level is higher than the expression base line level, and (d) a step of repeating the step (a) on the basis of the results of the step (c).

The characteristics and marked action and effects of the present invention other than those described above can be clear to those skilled in the art by making reference to the following embodiments of the present invention and drawings.

BRIEF DESCRIPTION OF THE DRAWINGS

FIG. 1 shows results of comprehensive gene expression data in DNA microarray experiments for healthy controls and mood disorder patients according to one embodiment of the present invention.

FIG. 2 shows results of confirmation experiments of RPL17 and RPL34 by qPCR that showed differences in expression in healthy controls and mood disorder patients according to one embodiment of the present invention.

FIGS. 3A-B (hereinafter sometimes referred to collectively as FIG. 3) show shows graphs showing measurement results of RPL17 and RPL34 by psychiatric illness using qPCR according to one embodiment of the present invention.

FIGS. 4A-B (hereinafter sometimes referred to collectively as FIG. 4) show results of ROC analyses confirming the improvement of the accuracy of detecting mood disorders by microarray analyses using RPL17 or RPL34 and genes supporting the same according to one embodiment of the present invention.

FIG. 5 shows graphs showing results confirming differences in expression of RPL17, RPL34 and CDKN1C in mood disorder patients and healthy controls by qPCR according to one embodiment of the present invention.

FIGS. 6A-C (hereinafter sometimes referred to collectively as FIG. 6) results of ROC analyses confirming the improvement of the accuracy of detecting mood disorders by qPCR using RPL17, RPL34 and CDKN1C according to one embodiment of the present invention.

FIGS. 7A-E (hereinafter sometimes referred to collectively as FIG. 7) show results of making a comparison among healthy controls, mood disorder patients having symptoms, and mood disorder patients whose symptoms have been remitted for the ribosomal protein gene group including RPL17 and RPL34 as well as for CDKN1C according to one embodiment of the present invention.

FIGS. 8A-C (hereinafter sometimes referred to collectively as FIG. 8) show shows graphs showing results of making a comparison between the resistance-to-stress group of healthy controls and the stress vulnerability group for the ribosomal protein gene group including RPL17 and RPL34 according to one embodiment of the present invention.

DETAILED DESCRIPTION OF THE INVENTION

The following describes one embodiment and examples according to the present invention with reference to drawings.

As described above, one embodiment of the present invention relates to a method for detecting mood disorders in a subject, the method comprising a step of measuring the expression levels of ribosomal protein genes, CDKN1C, or any combination thereof in the peripheral blood derived from the subject, wherein it is detected whether or not the subject has mood disorders on the basis of the measurement results.

That is, the present inventors found that the expression levels of ribosomal protein genes in the peripheral blood of mood disorder patients are high as compared with healthy controls and that the expression levels of CDKN1C in the peripheral blood of mood disorder patients are low as compared with healthy controls and thereby completed the abovementioned invention. The present inventors also found that the detection accuracy can be enhanced by combining those genes.

To determine whether or not a subject has mood disorders, the expression levels measured for the peripheral blood derived from the subject are compared with the expression levels (expression base line values) of the corresponding gene in the peripheral blood derived from healthy controls; and it can be shown that the subject has mood disorders if the expression levels increase in the subject more than in healthy controls when the measured genes are ribosomal protein genes or if the expression levels decline in the subject more than in healthy controls when the measured gene is CDKN1C.

As used herein, the term "mood disorders" are illnesses classified under major depression and bipolar disorders as representative examples and belong to a group of psychiatric disorders relating to mood. By way of example, these disorders include depression episodes mainly having symptoms of continuous sinking in mood, manic episodes having senses of refreshment, well-being and happiness and also having symptoms controlled by optimistic ideas, and illnesses having the symptoms of manic-depressive conditions in which both the depressive and manic symptoms are repeated, and are not particularly limited as long as they are illnesses having the abovementioned symptoms.

As used herein, the term "ribosomal protein gene" refers to a group of genes that express proteins constituting ribosomes and large and small subunits thereof. They are mainly indicated by abbreviations such as RPL (large unit) and RPS (small unit) and have branch numbers attached. By way of example, as used herein, the "ribosomal protein gene" includes, but is not limited to, RPL17, RPL23, RPL26, RPL31, RPL34, RPL36A, RPL7, RPL9, RPS15A, RPS24, RPS27, RPS3A or RPS7.

In one embodiment of the present invention, such ribosomal protein genes and CDKN1C can be used as gene markers used for detecting mood disorders. The ribosomal protein genes and CDKN1C can also be used as gene markers used for determining the effect of mood disorder treatment in mood disorder patients or determining stress vulnerability in subjects, as described below.

In one embodiment of the present invention, the accuracy of detecting mood disorders and the accuracy of determining therapeutic effects can be enhanced in subjects by combining a plurality (2, 3 or more) of genes, instead of using the abovementioned ribosomal protein genes and CDKN1C singly. For example, the accuracy of detecting mood disorders can be enhanced by measuring the expression levels of RPL34 and CDKN1C or the expression levels of RPL17 and CDKN1C in the peripheral blood derived from a subject at the time of detecting mood disorders in the subject, as compared with the case in which the expression levels of a single gene are measured. The abovementioned combination of genes may be a combination of ribosomal protein genes or a combination of a ribosomal protein gene and CDKN1C.

As used herein, the term "measuring the expression levels of genes" may be not only the measurement of the amount of mRNA or DNA of the gene but also the measurement of the amount of protein encoded by the gene. The effect of the present invention can be achieved by measuring the amount of any one of mRNA, cDNA and protein, and those skilled in the art can make a measurement by selecting any one of them appropriately.

Moreover, in one embodiment of the present invention, it is also possible to determine the effect of mood disorder treatment in mood disorder patients by measuring the expression levels of ribosomal protein genes and CDKN1C in the peripheral blood derived from mood disorder patients, as described above. In this case, by measuring the expression levels of ribosomal protein genes, CDKN1C or any combination of those genes in the peripheral blood derived from mood disorder patients, the effect of mood disorder treatment can be determined for the mood disorder patients on the basis of the measurement results.

Moreover, in one embodiment of the present invention, any gene may be measured, as long as the gene is expressed in the peripheral blood derived from mood disorder patients prior to a target treatment, wherein those mood disorder patients may be untreated patients or may be patients who already received one or more treatments.

Moreover, in one embodiment of the present invention, the effect of treating mood disorder patients may be determined by measuring the expression levels of corresponding genes prior to or subsequent to a target treatment used for the determination and then making a comparison between the expression levels prior to the treatment and the expression levels subsequent to the treatment. In this case, when the measured gene is a ribosomal protein gene, it is determined that therapeutic effects been attained if the expression levels of the gene measured prior to the treatment have declined after the treatment. On the other hand, when the measured gene is CDKN1C, it is determined that therapeutic effects have been attained if the expression levels of the gene measured prior to the treatment increased after the treatment.

Moreover, in one embodiment of the present invention, at the time of determining such therapeutic effects, the treatment of mood disorders and the determination of therapeutic effects may be repeated. By way of example, when the effect of the first treatment was determined in a manner described above and it was determined that no therapeutic effects were achieved or therapeutic effects were insufficient, so that additional treatments would be needed, the expression levels of the corresponding gene in the peripheral blood derived from the mood disorder patient after the additional treatment may be measured, and then the expression levels of the gene after the additional treatment may be compared with the expression levels of the gene after the initial treatment. The additional treatment and the determination of the result may be repeated as needed.

In one embodiment of the present invention, at the time of determining the effect of mood disorder treatment in mood disorder patients, the expression levels of a gene in the peripheral blood derived from the mood disorder patients may be compared with the expression levels of the corresponding gene in the peripheral blood derived from healthy controls, in addition to making a comparison between the expression levels prior to the treatment and the expression levels subsequent to the treatment in the mood disorder patients. For example, after performing mood disorder treatment for mood disorder patients, the expression levels of a gene in the peripheral blood derived from the mood disorder patients may be measured after the treatment, and then the result thereof may be compared with a base line value of expression levels (expression base line value) of the corresponding gene in healthy controls. When the measured gene is a ribosomal protein gene, it is determined that the treatment was insufficient if the expression levels of the gene in the mood disorder patients were higher than those of healthy controls (i.e., the gene were expressed more) after the treatment, so that the treatment can be continued or reinforced for the mood disorder patients. When the measured gene is CDKN1C, the treatment may be continued or reinforced likewise if the expression levels of the gene in the mood disorder patients were lower than those of healthy controls (i.e., the gene were expressed less) after the treatment.

On the other hand, when the measured gene is a ribosomal protein gene, it is determined that the treatment was very effective if the expression levels of the gene in the mood disorder patients after the treatment are equal to or lower than those of healthy controls (lower expression levels), so that the treatment for the mood disorder patients can be discontinued or mitigated. When the measured gene is CDKN1C, the treatment can be discontinued or mitigated likewise if the expression levels of the gene in the mood disorder patients after the treatment are equal to or higher than those of healthy controls (higher expression levels).

In one embodiment of the present invention, the abovementioned treatment and determination may be carried out at any timing, and the number of timings has no limitations.

In one embodiment of the present invention, it is also possible to determine stress vulnerability of a subject by measuring the expression levels of ribosomal protein genes in the peripheral blood derived from the subject as described above. In this case, it is determined whether or not the subject has stress vulnerability on the basis of measurement results after measuring the expression levels of ribosomal protein genes in the peripheral blood derived from the subject or any combination of those genes.

Moreover, in one embodiment of the present invention, at the time of determining the stress vulnerability of a subject, the expression levels of ribosomal protein genes in the peripheral blood derived from stress-resistant healthy controls (expression base line value) may be measured, and then those expression levels may be compared with the expression levels of ribosomal protein genes in the peripheral blood derived from the subject. In this case, when the expression levels of the genes in the peripheral blood derived from the subject are higher than those of the stress-resistant healthy controls (i.e., the genes are expressed more), it can be determined that the subject has stress vulnerability.

In one embodiment of the present invention, a solid support or kit for detecting mood disorders in subjects can be provided by combining primers, probes, or antibodies, which are used for confirming the expression of ribosomal protein genes and the CDKN1C gene as the abovementioned gene markers. In this case, the primers, probes, or antibodies may be created by various techniques well known in the genetic engineering and molecular biology fields and may have any length and size. Similarly, such a support or kit can be used to determine the result of treating mood disorders for mood disorder patients or determine the stress vulnerability of subjects.

EXAMPLES

The following describes the present invention in more details with reference to examples; however, the present invention is not limited by those examples.

The following describes experimental methods and materials used in the present invention. Although the following experimental methods are used in the present embodiment, the same results can be achieved by using other experimental methods as well.

1. Search for Marker Genes Used for Detecting Mood Disorders

To use as specimens for conducting microarray analyses, peripheral blood was collected at National Center of Neurology and Psychiatry from 25 mood disorder (major depression and bipolar depression) patients with morbid depressive symptoms and 25 health controls who matched the patients in terms of age and gender. Table 1 shows the result. As shown in Table 1, in the present example, there is no difference in age and gender between the health control group and the mood disorder group.

TABLE 1

Background information about microarray analysis specimens

|  | Healthy control group | Mood disorders group* |
|---|---|---|
| Number of cases | 25 | 25 |
| Age | 37.6 ± 10.5 | 37.0 ± 9.8 |
| Gender (female %) | 48.0 | 48.0 |
| HAM-D | — | 20.1 ± 4.9 |

*Mood disorders group Bipolar disorder 6 cases Major depression 19 cases

Next, RNA contained in the peripheral blood of those healthy controls and mood disorder patients was purified using a PAX gene blood RNA System. Then, Oligo DNA microarray (Agilent Corporation) experiments were conducted using this RNA to obtain extensive gene expression data.

The first DNA microarray experiment was conducted in 2009 for 13 cases of healthy controls and 13 cases of mood disorder patients, and the second DNA microarray experiment was conducted in 2011 for 12 cases of healthy controls and 12 cases of mood disorder patients; therefore data thus obtained had differences in batches due to the timing of those experiments. Therefore, the data thus obtained was corrected by a Combat method (see Biostatistics, 2007 January; 8(1): 118-27) (FIG. 1). As shown in FIG. 1, the disappearance of differences in batches by the Combat correction was confirmed. Data after the Combat correction was used in the following analyses.

Next, using Welch's t test, 154 probes (125 genes including those of increased expression levels and decreased expression levels in mood disorder patients) in which there were differences in expression between mood disorder patients and healthy controls were identified. The table 2 shows the result. In Table 2, False Discovery Rate (FDR: BH method)<0.25 and Fold Change >1.5 were used as threshold values used for extracting genes for differences in expression.

TABLE 2

Genes for differences in expression, mood disorders vs healthy control
UP by mood disorders

| Probe Name | Gene Symbol | Gene Name | Fold Change | p-value | FDR |
|---|---|---|---|---|---|
| A_24_P188878 | RPL34 | ribosomal protein L34 | 2.04 | 0.00321 | 0.20817 |
| A_23_P7229 | RPL34 | ribosomal protein L34 | 2.02 | 0.00285 | 0.20817 |
| A_24_P203909 | RPL34 | ribosomal protein L34 | 2.02 | 0.00301 | 0.20817 |
| A_24_P303118 | RPL34 | ribosomal protein L34 | 2.01 | 0.00110 | 0.20817 |
| A_23_P7221 | RPL34 | ribosomal protein L34 | 2.01 | 0.00169 | 0.20817 |
| A_32_P220127 | RPL34 | ribosomal protein L34 | 1.93 | 0.00759 | 0.20817 |
| A_32_P114215 | COMMD6 | COMM domain containing 6 | 1.93 | 0.00216 | 0.20817 |
| A_23_P1206 | RPS24 | ribosomal protein S24 | 1.87 | 0.00242 | 0.20817 |
| A_24_P106306 | RPL26L1 | ribosomal protein L26-like 1 | 1.83 | 0.00356 | 0.20817 |
| A_32_P136319 | RPL36A | ribosomal protein L36a | 1.80 | 0.01112 | 0.21250 |
| A_23_P434809 | S100A8 | S100 calcium binding protein A8 | 1.79 | 0.00298 | 0.20817 |
| A_32_P158746 | RPL17 | ribosomal protein L17 | 1.78 | 0.00178 | 0.20817 |
| A_32_P145153 | RPL31 | ribosomal protein L31 | 1.78 | 0.00298 | 0.20817 |
| A_23_P23074 | IFI44 | interferon-induced protein 44 | 1.77 | 0.01626 | 0.22431 |
| A_32_P186981 | RPL17 | ribosomal protein L17 | 1.77 | 0.00241 | 0.20817 |
| A_32_P21384 | RPL17 | ribosomal protein L17 | 1.76 | 0.00371 | 0.20817 |
| A_32_P173385 | XLOC_12_005691 |  | 1.75 | 0.00211 | 0.20817 |
| A_23_P43946 | SARNP | SAP domain containing ribonucleoprotein | 1.75 | 0.00079 | 0.20817 |
| A_24_P213783 | RPL31 | ribosomal protein L31 | 1.74 | 0.00339 | 0.20817 |
| A_32_P135818 | RPS3A | ribosomal protein S3A | 1.72 | 0.00298 | 0.20817 |
| A_32_P2333 | SUB1 | SUB1 homolog (S. cerevisiae) | 1.72 | 0.01319 | 0.21764 |
| A_24_P383999 | RPS3A | ribosomal protein S3A | 1.71 | 0.00404 | 0.20817 |
| A_23_P144497 | RPS3A | ribosomal protein S3A | 1.71 | 0.00489 | 0.20817 |
| A_32_P58074 | RPS3A | ribosomal protein S3A | 1.70 | 0.00512 | 0.20817 |
| A_32_P196483 | RPS3A | ribosomal protein S3A | 1.70 | 0.00412 | 0.20817 |
| A_23_P152002 | BCL2A1 | BCL2-related protein A1 | 1.69 | 0.00719 | 0.20817 |
| A_23_P59921 | SUB1 | SUB1 homolog (S. cerevisiae) | 1.69 | 0.01813 | 0.22933 |
| A_32_P208178 | RPS3A | ribosomal protein S3A | 1.68 | 0.00520 | 0.20817 |
| A_23_P38275 | RPL26 | ribosomal protein L26 | 1.68 | 0.01051 | 0.21250 |

TABLE 2-continued

Genes for differences in expression, mood disorders vs healthy control
UP by mood disorders

| Probe Name | Gene Symbol | Gene Name | Fold Change | p-value | FDR |
|---|---|---|---|---|---|
| A_23_P33045 | RPL26 | ribosomal protein L26 | 1.68 | 0.00821 | 0.20817 |
| A_32_P98313 | NDUFA4 | NADH dehydrogenase (ubiquinone) 1 alpha subcomplex, 4, 9 kDa | 1.68 | 0.00241 | 0.20817 |
| A_32_P20367 | RPS7 | ribosomal protein S7 | 1.68 | 0.00286 | 0.20817 |
| A_32_P10424 | LOC101060510 | uncharacterized LOC101060510 | 1.67 | 0.00126 | 0.20817 |
| A_23_P143958 | RPL22L1 | ribosomal protein L22-like 1 | 1.67 | 0.00531 | 0.20817 |
| A_23_P26713 | RPL23 | ribosomal protein L23 | 1.67 | 0.00642 | 0.20817 |
| A_23_P145777 | NDUFA4 | NADH dehydrogenase (ubiquinone) 1 alpha subcomplex, 4, 9 kDa | 1.67 | 0.00179 | 0.20817 |
| A_32_P93782 | RPL26 | ribosomal protein L26 | 1.65 | 0.01166 | 0.21506 |
| A_24_P29001 | LSM3 | LSM3 homolog, U6 small nuclear RNA associated (*S. cerevisiae*) | 1.65 | 0.00576 | 0.20817 |
| A_24_P126890 | RPL9 | ribosomal protein L9 | 1.64 | 0.00708 | 0.20817 |
| A_24_P169378 | RPS7 | ribosomal protein S7 | 1.63 | 0.00181 | 0.20817 |
| A_23_P141549 | RPS7 | ribosomal protein S7 | 1.63 | 0.00314 | 0.20817 |
| A_23_P64173 | CARD 16 | caspase recruitment domain family, member 16 | 1.63 | 0.00456 | 0.20817 |
| A_23_P110811 | COX7C | cytochrome c oxidase subunit VIIc | 1.62 | 0.00194 | 0.20817 |
| A_23_P7066 | RPL9 | ribosomal protein L9 | 1.62 | 0.00878 | 0.21027 |
| A_23_P83278 | CHMP5 | charged multivesicular body protein 5 | 1.61 | 0.00229 | 0.20817 |
| A_24_P15765 | RPS7P5 | ribosomal protein S7 pseudogene 5 | 1.60 | 0.00343 | 0.20817 |
| A_32_P30710 | RPL23 | ribosomal protein L23 | 1.60 | 0.00580 | 0.20817 |
| A_32_P190488 | XLOC_12_004312 | | 1.59 | 0.01790 | 0.22933 |
| A_32_P155364 | RPL7 | ribosomal protein L7 | 1.58 | 0.00790 | 0.20817 |
| A_24_P295543 | BLOC1S2 | biogenesis of lysosomal organelles complex-1, subunit 2 | 1.58 | 0.00107 | 0.20817 |
| A_32_P31182 | RPL7 | ribosomal protein L7 | 1.57 | 0.01064 | 0.21250 |
| A_23_P122233 | MRPL22 | mitochondrial ribosomal protein L22 | 1.57 | 0.00168 | 0.20817 |
| A_32_P44762 | TMA7 | translation machinery associated 7 homolog (*S. cerevisiae*) | 1.56 | 0.00304 | 0.20817 |
| A_23_P74629 | RPS27 | ribosomal protein S27 | 1.55 | 0.00617 | 0.20817 |
| A_24_P367191 | XLOC_12_015473 | | 1.55 | 0.01294 | 0.21702 |
| A_23_P8900 | COX6C | cytochrome c oxidase subunit VIc | 1.55 | 0.00241 | 0.20817 |
| A_23_P217609 | RPL36A | ribosomal protein L36a | 1.54 | 0.02381 | 0.24020 |
| A_24_P148235 | RPS27 | ribosomal protein S27 | 1.53 | 0.00662 | 0.20817 |
| A_23_P205281 | C14orf2 | chromosome 14 open reading frame 2 | 1.53 | 0.00212 | 0.20817 |
| A_24_P124992 | PSMA4 | proteasome (prosome, macropain) subunit, alpha type, 4 | 1.53 | 0.01031 | 0.21250 |
| A_32_P7118 | PSMC6 | proteasome (prosome, macropain) 26S subunit, ATPase, 6 | 1.52 | 0.00132 | 0.20817 |
| A_32_P175580 | RPS15A | ribosomal protein S15a | 1.52 | 0.00143 | 0.20817 |
| A_24_P232856 | RPL9 | ribosomal protein L9 | 1.52 | 0.01348 | 0.21873 |
| A_23_P91230 | SLPI | secretory leukocyte peptidase inhibitor | 1.52 | 0.01233 | 0.21658 |
| A_24_P381625 | PSMC6 | proteasome (prosome, macropain) 26S subunit, ATPase, 6 | 1.52 | 0.00139 | 0.20817 |
| A_24_P192805 | CARD17 | caspase recruitment domain family, member 17 | 1.52 | 0.01268 | 0.21658 |
| A_23_P25735 | PSMA6 | proteasome (prosome, macropain) subunit, alpha type, 6 | 1.51 | 0.00307 | 0.20817 |
| A_23_P18325 | PDCD10 | programmed cell death 10 | 1.51 | 0.00307 | 0.20817 |

TABLE 2-continued

Genes for differences in expression, mood disorders vs healthy control
UP by mood disorders

| Probe Name | Gene Symbol | Gene Name | Fold Change | p-value | FDR |
|---|---|---|---|---|---|
| A_23_P98382 | TIMM8B | translocase of inner mitochondrial membrane 8 homolog B (yeast) | 1.51 | 0.00261 | 0.20817 |
| A_32_P336445 | HINT1 | histidine triad nucleotide binding protein 1 | 1.51 | 0.00545 | 0.20817 |
| A_23_P94230 | LY96 | lymphocyte antigen 96 | 1.51 | 0.01044 | 0.21250 |
| A_32_P43217 | PSMA6 | proteasome (prosome, macropain) subunit, alpha type, 6 | 1.51 | 0.00498 | 0.20817 |
| | | Ribosomal protein genes Down by mood disorders | | | |
| A_23_P44533 | PLCXD2 | phosphatidylinositol-specific phospholipase C, X domain containing 2 | −2.32 | 0.00646 | 0.20817 |
| A_24_P372643 | SLC22A18AS | solute carrier family 22 (organic cation transporter), member 18 antisense | −2.15 | 0.01841 | 0.22933 |
| A_24_P311036 | MYOG | myogenin (myogenic factor 4) | −2.12 | 0.02123 | 0.23658 |
| A_23_P218505 | LHB | luteinizing hormone beta polypeptide | −2.11 | 0.01948 | 0.22992 |
| A_23_P62361 | UBL4A | ubiquitin-like 4A | −2.06 | 0.02174 | 0.23812 |
| A_23_P130761 | DBP | D site of albumin promoter (albumin D-box) binding protein | −2.06 | 0.00456 | 0.20817 |
| A_23_P21747 | CABP5 | calcium binding protein 5 | −2.04 | 0.01861 | 0.22933 |
| A_24_P153734 | SEC16B | SEC 16 homolog B (S. cerevisiae) | −2.00 | 0.02005 | 0.23364 |
| A_23_P335988 | UBL4A | ubiquitin-like 4A | −2.00 | 0.01910 | 0.22967 |
| A_24_P23636 | PCLO | piccolo presynaptic cytomatrix protein | −1.96 | 0.00623 | 0.20817 |
| A_23_P218269 | TAOK2 | TAO kinase 2 | −1.95 | 0.01605 | 0.22415 |
| A_23_P167537 | CPLX2 | complexin 2 | −1.93 | 0.01693 | 0.22648 |
| A_23_P28595 | DLX2 | distal-less homeobox 2 | −1.93 | 0.00530 | 0.20817 |
| A_23_P39453 | MEX3D | mex-3 RNA binding family member D | −1.92 | 0.01467 | 0.22027 |
| A_24_P311063 | ANKRD65 | ankyrin repeat domain 65 | −1.92 | 0.01063 | 0.21250 |
| A_24_P163574 | GIGYF1 | GRB10 interacting GYF protein 1 | −1.91 | 0.00744 | 0.20817 |
| A_23_P168928 | CYP11B1 | cytochrome P450, family 11, subfamily B, polypeptide 1 | −1.90 | 0.01850 | 0.22933 |
| A_23_P363196 | TCL6 | T-cell leukemia/lymphoma 6 (non-protein coding) | −1.89 | 0.00710 | 0.20817 |
| A_23_P137046 | NYX | nyctalopin | −1.88 | 0.00570 | 0.20817 |
| A_23_P20075 | NPC1L1 | NPC1-like 1 | −1.85 | 0.00552 | 0.20817 |
| A_23_P20804 | FAM219A | family with sequence similarity 219, member A | −1.85 | 0.00691 | 0.20817 |
| A_23_P41365 | SMR3A | submaxillary gland androgen regulated protein 3 A | −1.84 | 0.02318 | 0.23894 |
| A_23_P94942 | SHARPIN | SHANK-associated RH domain interactor | −1.83 | 0.00879 | 0.21027 |
| A_23_P123393 | KCNQ3 | potassium voltage-gated channel, KQT-like subfamily, member 3 | −1.83 | 0.00414 | 0.20817 |
| A_23_P258164 | CORT | cortistatin | −1.82 | 0.02042 | 0.23449 |
| A_23_P132139 | C21orf58 | chromosome 21 open reading frame 58 | −1.81 | 0.00689 | 0.20817 |
| A_23_P82088 | NRN1 | neuritin 1 | −1.80 | 0.00743 | 0.20817 |
| A_23_P86874 | KCNK7 | potassium channel, subfamily K, member 7 | −1.79 | 0.01560 | 0.22153 |
| A_23_P17330 | UCKL1 | uridine-cytidine kinase 1-like 1 | −1.78 | 0.00624 | 0.20817 |
| A_23_P76992 | PGF | placental growth factor | −1.76 | 0.00556 | 0.20817 |
| A_32_P218228 | FAM109B | family with sequence similarity 109, member B | −1.76 | 0.01335 | 0.21764 |
| A_24_P416055 | FAM103A1 | family with sequence similarity 103, member A1 | −1.74 | 0.01104 | 0.21250 |
| A_23_P135848 | PROP1 | PROP paired-like homeobox 1 | −1.73 | 0.01609 | 0.22427 |
| A_23_P120513 | C20orf141 | chromosome 20 open reading frame 141 | −1.72 | 0.02174 | 0.23812 |
| A_23_P142835 | DCTN1 | dynactin 1 | −1.72 | 0.02291 | 0.23894 |
| A_32_P448360 | ASB16-AS1 | ASB16 antisense RNA1 | −1.71 | 0.02354 | 0.24020 |
| A_23_P27424 | ZNF418 | zinc finger protein 418 | −1.71 | 0.02392 | 0.24020 |
| A_23_P14302 | LINC00341 | long intergenic non-protein coding RNA 341 | −1.70 | 0.01216 | 0.21658 |
| A_23_P84929 | SLC38A5 | solute carrier family 38, member 5 | −1.70 | 0.00299 | 0.20817 |
| A_23_P393627 | KLF14 | Kruppel-like factor 14 | −1.69 | 0.01868 | 0.22936 |

TABLE 2-continued

Genes for differences in expression, mood disorders vs healthy control
UP by mood disorders

| Probe Name | Gene Symbol | Gene Name | Fold Change | p-value | FDR |
|---|---|---|---|---|---|
| A_23_P77000 | VASH1 | vasohibin 1 | −1.69 | 0.01685 | 0.22648 |
| A_24_P219094 | SIPA1L1 | signal-induced proliferation-associated 1 like 1 | −1.68 | 0.00478 | 0.20817 |
| A_23_P160359 | EPB41 | erythrocyte membrane protein band 4.1 | −1.68 | 0.00382 | 0.20817 |
| A_32_P346000 | LOC100507351 | uncharacterized LOC100507351 | −1.67 | 0.00761 | 0.20817 |
| A_23_P51679 | MEF2D | myocyte enhancer factor 2D | −1.67 | 0.00721 | 0.20817 |
| A_24_P239183 | MUC4 | mucin 4, cell surface associated | −1.66 | 0.02160 | 0.23754 |
| A_23_P398574 | BCAM | basal cell adhesion molecule (Lutheran blood group) | −1.66 | 0.00958 | 0.21250 |
| A_24_P374962 | STAG3L2 | stromal antigen 3-like 2 (pseudogene) | −1.66 | 0.02566 | 0.24398 |
| A_23_P5221 | ZNF333 | zinc finger protein 333 | −1.64 | 0.01224 | 0.21658 |
| A_23_P74330 | LINC00626 | long intergenic non-protein coding RNA 626 | −1.64 | 0.02480 | 0.24386 |
| A_24_P99963 | CSNK1G2 | casein kinase 1, gamma 2 | −1.63 | 0.01392 | 0.22024 |
| A_24_P384397 | RAVER1 | ribonucleoprotein, PTB-binding 1 | −1.62 | 0.00645 | 0.20817 |
| A_24_P119036 | TOX3 | TOX high mobility group box family member 3 | −1.62 | 0.02750 | 0.24922 |
| A_23_P139162 | CD6 | CD6 molecule | −1.61 | 0.02390 | 0.24020 |
| A_24_P288298 | KIR2DL4 | killer cell immunoglobulin-like receptor, two domains, long cytoplasmic tail, 4 | −1.61 | 0.01489 | 0.22027 |
| A_23_P11071 | PORCN | porcupine homolog (Drosophila) | −1.61 | 0.02412 | 0.24098 |
| A_23_P25224 | YBX3 | Y box binding protein 3 | −1.60 | 0.00109 | 0.20817 |
| A_23_P334186 | MEF2D | myocyte enhancer factor 2D | −1.60 | 0.02147 | 0.23687 |
| A_23_P108662 | MOGS | mannosyl-oligosaccharide glucosidase | −1.59 | 0.01610 | 0.22427 |
| A_23_P129829 | ORMDL3 | ORMDL sphingolipid biosynthesis regulator 3 | −1.59 | 0.00995 | 0.21250 |
| A_23_P17880 | DNAL4 | dynein, axonemal, light chain 4 | −1.59 | 0.02404 | 0.24066 |
| A_24_P945293 | CHMP3 | charged multivesicular body protein 3 | −1.59 | 0.02498 | 0.24386 |
| A_23_P75867 | OR10A4 | olfactory receptor, family 10, subfamily A, member 4 | −1.58 | 0.02555 | 0.24386 |
| A_24_P368943 | EVX1 | even-skipped homeobox 1 | −1.57 | 0.02553 | 0.24386 |
| A_23_P80382 | PRR5 | proline rich 5 (renal) | −1.57 | 0.01381 | 0.22005 |
| A_23_P113204 | FGF3 | fibroblast growth factor 3 | −1.56 | 0.02530 | 0.24386 |
| A_23_P107465 | KRT31 | keratin 31 | −1.56 | 0.02193 | 0.23812 |
| A_23_P36364 | THY1 | Thy-1 cell surface antigen | −1.56 | 0.02278 | 0.23890 |
| A_23_P23839 | LGR6 | leucine-rich repeat containing G protein-coupled receptor 6 | −1.56 | 0.01851 | 0.22933 |
| A_23_P89691 | SDK2 | sidekick cell adhesion molecule 2 | −1.56 | 0.02063 | 0.23449 |
| A_23_P168584 | POMZP3 | POM121 and ZP3 fusion | −1.55 | 0.02544 | 0.24386 |
| A_23_P404685 | LCE1A | late cornified envelope 1A | −1.55 | 0.01332 | 0.21764 |
| A_32_P13348 | HIPK2 | homeodomain interacting protein kinase 2 | −1.55 | 0.00872 | 0.21009 |
| A_24_P234105 | GLTPD1 | glycolipid transfer protein domain containing 1 | −1.54 | 0.01205 | 0.21658 |
| A_24_P341019 | TMEM230 | transmembrane protein 230 | −1.53 | 0.01904 | 0.22967 |
| A_24_P666340 | LOC101927507 | uncharacterized LOC101927507 | −1.53 | 0.02422 | 0.24125 |
| A_23_P113682 | SLC34A3 | solute carrier family 34 (type II sodium/phosphate contransporter), member 3 | −1.53 | 0.02312 | 0.23894 |
| A_24_P14485 | RBM38 | RNA binding motif protein 38 | −1.52 | 0.01977 | 0.23223 |
| A_24_P23400 | SLC6A8 | solute carrier family 6 (neurotransmitter transporter), member 8 | −1.52 | 0.01748 | 0.22839 |
| A_23_P89981 | CYP2F1 | cytochrome P450, family 2, subfamily F, polypeptide 1 | −1.52 | 0.01926 | 0.22982 |
| A_23_P79086 | NFKBIB | nuclear factor of kappa light polypeptide gene enhancer in B-cells inhibitor, beta | −1.52 | 0.01577 | 0.22184 |
| A_23_P250156 | IGF2BP2 | insulin-like growth factor 2 mRNA binding protein 2 | −1.51 | 0.01255 | 0.21658 |

The present inventors further conducted functional analyses (Gene Ontology Analyses) for each of gene groups having increased expression and decreased expression in order to narrow down genes that could be candidates for molecular markers and search for genes that changed their expressions as a result of functional changes peculiar to mood disorder patients. Consequently, no significant change was detected in gene groups having expression levels declined in mood disorder patients as compared with healthy controls, while ribosomal protein-related GO Term was detected as a significant function in gene groups having expression levels increased (Table 3).

TABLE 3

Functional analyses of genes for differences in expression (analytical results of gene ontology)
UP by mood disorders

| GO biological process complete | RefList | TargetList | P-value |
| --- | --- | --- | --- |
| SRP-dependent cotranslational protein targeting to membrane (GO:0006614) | 93 | 13 | 2.33E−17 |
| cotranslational protein targeting to membrane (GO:0006613) | 99 | 13 | 5.22E−17 |
| protein targeting to ER (GO:0045047) | 102 | 13 | 7.66E−17 |
| establishment of protein localization to endoplasmic reticulum (GO:0072599) | 106 | 13 | 1.26E−16 |
| viral transcription (GO:0019083) | 114 | 13 | 3.21E−16 |
| nuclear-transcribed mRNA catabolic process, nonsense-mediated decay (GO:0000184) | 119 | 13 | 5.57E−16 |
| protein localization to endoplasmic reticulum (GO:0070972) | 126 | 13 | 1.16E−15 |
| viral gene expression (GO:0019080) | 128 | 13 | 1.42E−15 |
| protein targeting to membrane (GO:0006612) | 133 | 13 | 2.32E−15 |
| translational initiation (GO:0006413) | 143 | 13 | 5.89E−15 |
| nuclear-transcribed mRNA catabolic process (GO:0000956) | 198 | 14 | 6.95E−15 |
| mRNA catabolic process (GO:0006402) | 211 | 14 | 1.67E−14 |
| translation (GO:0006412) | 382 | 16 | 5.13E−14 |
| RNA catabolic process (GO:0006401) | 238 | 14 | 8.72E−14 |
| peptide biosynthetic process (GO:0043043) | 411 | 16 | 1.60E−13 |
| nucleobase-containing compound catabolic process (GO:0034655) | 357 | 15 | 6.62E−13 |
| protein targeting (GO:0006605) | 280 | 14 | 8.08E−13 |
| establishment of protein localization to membrane (GO:0090150) | 215 | 13 | 1.08E−12 |
| amide biosynthetic process (GO:0043604) | 481 | 16 | 1.84E−12 |
| cytoplasmic translation (GO:0002181) | 46 | 9 | 2.57E−12 |
| heterocycle catabolic process (GO:0046700) | 402 | 15 | 3.73E−12 |
| cellular nitrogen compound catabolic process (GO:0044270) | 404 | 15 | 4.01E−12 |
| aromatic compound catabolic process (GO:0019439) | 416 | 15 | 6.14E−12 |
| ribosome biogenesis (GO:0042254) | 333 | 14 | 8.60E−12 |
| peptide metabolic process (GO:0006518) | 538 | 16 | 1.04E−11 |
| rRNA processing (GO:0006364) | 259 | 13 | 1.16E−11 |
| organic cyclic compound catabolic process (GO:1901361) | 450 | 15 | 1.92E−11 |
| ribonucleoprotein complex biogenesis (GO:0022613) | 465 | 15 | 3.09E−11 |
| rRNA metabolic process (GO:0016072) | 286 | 13 | 4.07E−11 |
| establishment of protein localization to organelle (GO:0072594) | 385 | 14 | 6.17E−11 |

In a specimen group different from the group in which microarray analyses were conducted (mood disorder patients: 14 cases of patients, healthy controls: 11 cases), the qPCR verification was conducted for RPL 17 and RPL34, which had particularly large differences in expression, from among the abovementioned ribosomal protein gene groups (FIG. 2).

As a result, it was also confirmed in this qPCR verification using samples independent of microarray analyses that there were significant differences between the mood disorder patient group and the health control group with regard to those two genes, i.e., RPL17 and RPL34. The fact that significant differences were found even when different specimens and different testing methods were used shows that those two genes, i.e., RPL17 and RPL34 are highly reliable as molecular markers showing mood disorders.

Furthermore, the qPCR verification was conducted for cases separately obtained, i.e., 43 cases of schizophrenia, 48 cases of major depression, 46 cases of bipolar depression and 46 cases of healthy controls to find that RPL17 and RPL34 characteristically changed in mood disorders (major depression and bipolar depression) (FIG. 3). The results of the abovementioned verification suggest that mood disorders can objectively be detected by measuring the expression levels of RPL17 and RPL34 genes in whole blood.

On the other hand, the expression levels of RPL17 and RPL34 in schizophrenia patients were substantially the same as those of healthy controls, which shows that RPL17 and RPL34 can be used for distinguishing mood disorder patients from other psychiatric patients.

2. Search for Genes Used for Enhancing the Accuracy of Detecting Mood Disorders from Among Marker Genes Used for Detecting Mood Disorders Subsequently, to enhance the accuracy of the mood disorder detection marker genes found above, the present inventors searched for genes that could enhance the mood disorder detection accuracy of RPL17 and RPL34 from 221 probes (182 genes) in which differences were found at FDR (BH method)<0.25 and Fold Change >1.4 in the Welch's t test using microarray data of mood disorder patients (25 cases) and healthy controls (25 cases).

First, to sort out genes having information independent of RPL17 and RPL34, genes whose absolute values of correlation coefficients with RPL17 and RPL34 were smaller than 0.4 as compared with the abovementioned two gene (i.e., YBX1, HIP1, CDKN1C, SLPI, and IFI44) were selected as candidate genes (Table 4). That is, those candidate genes are expressed with significant differences between mood disorder patients and healthy controls in microarray analyses and have a low correlation with the mood disorder detection marker genes, i.e., RPL17 and RPL34, and therefore those candidate genes must be changing the expression levels thereof by some factors independent of RPL17 and RPL34.

TABLE 4

Candidate genes supporting RP17 and RP34

| ProbeName | GeneSymbol | GeneName | Results of comparison between 25 cases of mood disorders and 25 cases of healthy control | | | Results of correlation analysis of expression levels of RPL17 and RPL34 | |
|---|---|---|---|---|---|---|---|
| | | | Fold Change | p-value | FDR | Pearson's R with RPL17 | Pearson's R with RPL34 |
| A_24_P101391 | YBX1 | Y box binding protein 1 | −1.45 | 0.00286 | 0.20817 | −0.377 | −0.380 |
| A_24_P55391 | HIP1 | huntingtin interacting protein 1 | −1.42 | 0.00813 | 0.20817 | −0.345 | −0.313 |
| A_23_P428129 | CDKN1C | cyclin-dependent kinase inhibitor 1C (p57, Kip2) | −1.45 | 0.00295 | 0.20817 | −0.013 | 0.004 |
| A_23_P91230 | SLPI | secretory leukocyte peptidase inhibitor | 1.52 | 0.01233 | 0.21658 | 0.215 | 0.239 |
| A_23_P23074 | IFI44 | interferon-induced protein 44 | −1.77 | 0.01626 | 0.22431 | 0.343 | 0.350 |

Then, multiple logistic regression analyses were conducted using RPL17 or RPL34 and each of the candidate genes, i.e., YBX1, HIP1, CDKN1C, SLPI, and IFI44, and then diagnostic accuracy analyses (ROC analyses) were performed using the probability of mood disorders thus obtained. FIG. 4 shows the result. As shown in FIG. 4, it is clear that for both genes (RPL17 and RPL34), CDKN1C can enhance the mood disorder detection accuracy of RPL17 or RPL34 most from among the candidate genes.

Subsequently, qPCR data about RPL17, RPL34 and CDKN1C was obtained from 124 cases of mood disorder patients and 82 cases of healthy controls including the abovementioned specimens. As a result, in qPCR analyses, significant differences in expression were found between the mood disorder patient group and the healthy control group (declines in expression) in not only RPL17 and RPL34 but CDKN1C as well (FIG. 5). This shows that mood disorders can objectively be detected using CDKN1C alone, i.e., without using it together with RPL17 or RPL34.

3. Enhancement of Accuracy for Detecting Mood Disorders by the Concomitant Use of Marker Genes Used for Detecting Mood Disorders The detection accuracy of mood disorders was verified in the specimen group in which qPCR data about CDKN1C was obtained, using each of RPL17, RPL34 and CDKN1C and any combination thereof (FIG. 6). As shown in FIG. 6, mood disorders can be detected with a certain level of accuracy even when each of RPL17, RPL34 and CDKN1C is used singly; however, it is shown that the detection accuracy of mood disorders can further be enhanced by making a measurement together with CDKN1C as compared with the case in which the expression levels of RPL17 or RPL34 were measured singly in whole blood.

4. Determination of Effects of Mood Disorder Treatment with Marker Genes Used for Detecting Mood Disorders Subsequently, to verify whether or not the genes found as the mood disorder detection markers were related to the effect of treating mood disorder patients, the present inventors collected peripheral blood from 54 cases of mood disorders patients having morbid depressive symptoms (major depression: 47 cases, bipolar depression: 7 cases), 14 cases of mood disorders patients having remitted depressive symptoms (major depression: 12 cases, bipolar depression: 2 cases), and 54 cases of healthy controls and then obtained extensive gene expression data using microarray analyses by a method similar to that described above in order to confirm the expression levels of ribosomal protein genes including RPL17 and RPL34 as well as the expression levels of CDKN1C. FIG. 7 shows the result. As shown in FIG. 7, the remitted depressive symptom group showed the tendency of lowering the expression levels of ribosomal protein genes including RPL17 and RPL34, as compared with the depressive symptom group. Moreover, in the remitted depressive symptom group, the average value of each gene of the ribosomal protein gene group and CDKN1C was in between the depressive symptom group and the healthy control group. This shows that the effect of treating mood disorders can be determined by measuring the expression levels of each gene of the ribosomal protein gene group and CDKN1C in whole blood.

5. Determination of Stress Vulnerability with Marker Genes Used for Detecting Mood Disorders It is known that people who are less resistant to stress are at higher risk of having mood disorders including major depression. Accordingly, the present inventors verified whether or not the gene markers identified above and used for detecting mood disorders were related to the stress vulnerability of healthy individuals.

From healthy individuals, 20 cases of a Vulnerable Group in which subjects were vulnerable to stress and 20 cases of a Resistant Group in which subjects were resistant to stress were selected. The peripheral blood of these subjects was used to obtain extensive gene expression data using microarrays; the expression levels of the ribosomal protein gene group including RPL17 and RPL34 as well as the expression levels of CDKN1C were confirmed; and then a comparison was made between those groups. FIG. 8 shows the result. As shown in FIG. 8, CDKN1C did not show any difference between the Vulnerable Group and the Resistant Group; however, significant differences in expression were found between the Vulnerable Group and the Resistant Group in the ribosomal protein gene group including RPL17 and RPL34. This shows that the stress vulnerability of a subject can be determined by measuring the expression levels of each gene in the ribosomal protein gene group using the peripheral blood of the subject.

It goes without saying that the present invention may be modified in other various manners; that is, the present invention is not limited to the abovementioned one embodiment but can be modified in various ways without departing from the scope of the present invention.

What is claimed is:

1. A method of treating major depression or a bipolar disorder in a patient, comprising
    1) Measuring mRNA expression levels of at least one of RPL17, RPL23, RPL26, RPL31, RPL34, RPL36A, RPL7, RPL9, RPS15A, RPS24, RPS27 RPS3A, RPS7, and CDKN1C in peripheral blood derived from the patient, and
    2) Either A) or B):
        A) observing higher mRNA expression levels of at least one of RPL17, RPL23, RPL26, RPL31, RPL34, RPL36A, RPL7, RPL9, RPS15A, RPS24, RPS27, RPS3A and RPS7 relative to corresponding mRNA expression levels in peripheral blood of a healthy control thereby detecting that the patient has major depression or a bipolar disorder; or
        B) observing a lower mRNA expression level of CDKN1C relative to a corresponding mRNA expression level of CDKN1C in peripheral blood of a healthy control thereby detecting that the patient has major depression or a bipolar disorder; and
    3) administering treatment to the patient for the major depression or the bipolar disorder.

2. The method according to claim 1, wherein the step of measuring measures the expression levels of RPL34 and CDKN1C or the expression levels of RPL17 and CDKN1C.

3. A method of continuing or discontinuing treatment of major depression or a bipolar disorder in a patient, comprising steps of
    (a) measuring mRNA expression levels of at least one of RPL17, RPL23, RPL26, RPL31, RPL34, RPL36A, RPL7, RPL9, RPS15A, RPS24, RPS27, RPS3A, RPS7 and CDKN1C, in peripheral blood derived from the patient prior to or during treatment,
    (b) measuring corresponding mRNA expression levels in peripheral blood derived from the patient after treatment and
    (c) comparing the measurement results of the step (a) and the measurement results of the step (b), and
    (d)(i) determining that the treatment has been effective and thereby discontinuing treatment, or
    (d)(ii) determining that the treatment has been ineffective and thereby continuing treatment;
    wherein it is determined that the treatment has been effective when (i) the measured mRNA expression levels of at least one of RPL17, RPL23, RPL26, RPL31, RPL34, RPL36A, RPL7, RPL9, RPS15A, RPS24, RPS27, RPS3A, and RPS7 in the step (b) are lower than the corresponding expression levels measured in the step (a), or (ii) the measured mRNA expression level of CDKN1C in the step (b) is higher than the measured mRNA expression level of CDKN1C in the step (a); and
    wherein it is determined that the treatment has been ineffective when (i) the measured mRNA expression levels of at least one of RPL17, RPL23, RPL26, RPL31, RPL34, RPL36A, RPL7, RPL9, RPS15A, RPS24, RPS27, RPS3A, and RPS7 in the step (b) are higher than the corresponding measured expression levels in the step (a), or (ii) the measured mRNA expression level of CDKN1C in the step (b) is lower than the measured mRNA expression level of CDKN1C in the step (a).

4. The method according to claim 3, further comprising steps of:
    (e) measuring expression levels of corresponding genes in peripheral blood derived from the patient after an additional treatment provided based on the results of the step (d)(ii), and
    (f) making a comparison between the measurement results of the step (b) and the measurement results of the step (e), wherein the step (e) is repeated when the additional treatment is determined to be ineffective based on this comparison of step (f).

5. The method according to claim 3, wherein the step (a) measures the expression levels of RPL34 and CDKN1C or the expression levels of RPL17 and CDKN1C.

6. A method of treating major depression or a bipolar disorder in a patient, comprising a step of:
    treating major depression or a bipolar disorder in a patient, when
        A) said patient has higher mRNA expression levels of at least one of RPL17, RPL23, RPL26, RPL31, RPL34, RPL36A, RPL7, RPL9, RPS15A, RPS24, RPS27, RPS3A and RPS7 relative to corresponding mRNA expression levels in peripheral blood of a healthy control; or
        B) said patient has lower mRNA expression levels of CDKN1C relative to a mRNA expression level of CDKN1C in peripheral blood of a healthy control.

* * * * *